(12) United States Patent
Carlsson et al.

(10) Patent No.: US 7,563,578 B2
(45) Date of Patent: *Jul. 21, 2009

(54) METHOD FOR IN VITRO MOLECULAR EVOLUTION OF PROTEIN FUNCTION

(75) Inventors: Roland Carlsson, Lund (SE);
Ann-Christin Malmborg Hager, Helsingborg (SE); Christina Furebring, Lund (SE); Carl Borrebaeck, Hjarup (SE)

(73) Assignee: Alligator Bioscience AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/858,429

(22) Filed: Sep. 20, 2007

(65) Prior Publication Data

US 2008/0248533 A1    Oct. 9, 2008

Related U.S. Application Data

(63) Continuation of application No. 11/185,044, filed on Jul. 20, 2005, now Pat. No. 7,282,334, which is a continuation of application No. 09/734,801, filed on Dec. 12, 2000, now Pat. No. 6,958,213.

(51) Int. Cl.
*C12Q 1/68* (2006.01)
*C12P 19/34* (2006.01)
*C07H 21/04* (2006.01)

(52) U.S. Cl. .................. 435/6; 435/91.2; 536/24.33

(58) Field of Classification Search .................. 435/6; 536/24.33
See application file for complete search history.

(56) References Cited

U.S. PATENT DOCUMENTS

| | | |
|---|---|---|
| 4,683,202 A | 7/1987 | Mullis |
| 4,888,286 A | 12/1989 | Crea |
| 4,965,188 A | 10/1990 | Mullis et al. |
| 4,994,368 A | 2/1991 | Goodman et al. |
| 5,023,171 A | 6/1991 | Ho et al. |
| 5,043,272 A | 8/1991 | Hartley |
| 5,223,408 A | 6/1993 | Goeddel et al. |
| 5,252,479 A | 10/1993 | Srivastava |
| 5,270,170 A | 12/1993 | Schatz et al. |
| 5,338,665 A | 8/1994 | Schatz et al. |
| 5,491,074 A | 2/1996 | Aldwin et al. |
| 5,498,530 A | 3/1996 | Schatz et al. |
| 5,502,167 A | 3/1996 | Waldmann et al. |
| 5,512,463 A | 4/1996 | Stemmer |
| 5,514,568 A | 5/1996 | Stemmer |
| 5,521,291 A | 5/1996 | Curiel et al. |
| 5,573,907 A | 11/1996 | Carrino et al. |
| 5,605,793 A | 2/1997 | Stemmer |
| 5,712,089 A | 1/1998 | Borrebaeck et al. |
| 5,714,316 A | 2/1998 | Weiner et al. |
| 5,723,323 A | 3/1998 | Kauffman et al. |
| 5,733,731 A | 3/1998 | Schatz et al. |
| 5,733,753 A | 3/1998 | Jorgensen |
| 5,763,192 A | 6/1998 | Kauffman et al. |
| 5,798,208 A | 8/1998 | Crea |
| 5,811,238 A | 9/1998 | Stemmer et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,830,650 A | 11/1998 | Crea |
| 5,830,696 A | 11/1998 | Short |
| 5,830,721 A | 11/1998 | Stemmer et al. |
| 5,834,252 A | 11/1998 | Stemmer et al. |
| 5,837,458 A | 11/1998 | Minshull et al. |
| 5,858,657 A | 1/1999 | Winter et al. |
| 5,858,725 A | 1/1999 | Crowe et al. |
| 5,871,907 A | 2/1999 | Winter et al. |
| 5,925,544 A | 7/1999 | Jorgensen |
| 5,928,905 A | 7/1999 | Stemmer et al. |
| 5,939,250 A | 8/1999 | Short |
| 5,965,408 A | 10/1999 | Short |
| 5,969,108 A | 10/1999 | McCafferty et al. |
| 5,976,862 A | 11/1999 | Kauffman et al. |
| 6,096,548 A | 8/2000 | Stemmer |
| 6,117,679 A | 9/2000 | Stemmer |

(Continued)

FOREIGN PATENT DOCUMENTS

EP    0368684    5/1990

(Continued)

OTHER PUBLICATIONS

Lewin B, "Genes V" (1994), p. 647.

(Continued)

*Primary Examiner*—Suryaprabha Chunduru
(74) *Attorney, Agent, or Firm*—Dann Dorfman Herrell and Skillman; Robert C. Netter, Jr.

(57) ABSTRACT

The invention provides a method for generating a polynucleotide sequence or population of sequences from parent single stranded polynucleotide sequences encoding one or more protein motifs, comprising the steps of
  a) providing single stranded DNA constituting plus and minus strands of parent polynucleotide sequences;
  b) digesting the single stranded polynucleotide sequences with a nuclease other than DNase I to generate populations of single stranded fragments;
  c) contacting said fragments generated from the plus strands with fragments generated from the minus strands and optionally, adding primer sequences that anneal to the 3' and 5' ends of at least one of the parent polynucleotides under annealing conditions;
  d) amplifying the fragments that anneal to each other to generate at least one polynucleotide sequence encoding one or more protein motifs having altered characteristics as compared to the one or more protein motifs encoded by said parent polynucleotides.

6 Claims, 5 Drawing Sheets

U.S. PATENT DOCUMENTS

| | | | |
|---|---|---|---|
| 6,132,970 | A | 10/2000 | Stemmer |
| 6,143,527 | A | 11/2000 | Pachuk et al. |
| 6,153,410 | A | 11/2000 | Arnold et al. |
| 6,156,511 | A | 12/2000 | Schatz et al. |
| 6,159,687 | A | 12/2000 | Vind |
| 6,159,688 | A | 12/2000 | Borchert et al. |
| 6,159,690 | A * | 12/2000 | Borrebaeck et al. ............ 435/6 |
| 6,165,793 | A | 12/2000 | Stemmer |
| 6,171,820 | B1 | 1/2001 | Short |
| 6,177,263 | B1 | 1/2001 | Arnold et al. |
| 6,180,406 | B1 | 1/2001 | Stemmer |
| 6,238,884 | B1 | 5/2001 | Short et al. |
| 6,251,604 | B1 | 6/2001 | Lietz |
| 6,251,674 | B1 | 6/2001 | Tobin et al. |
| 6,265,201 | B1 | 7/2001 | Wackett et al. |
| 6,277,638 | B1 | 8/2001 | Stemmer |
| 6,287,861 | B1 | 9/2001 | Stemmer et al. |
| 6,287,862 | B1 | 9/2001 | delCardayre et al. |
| 6,291,165 | B1 | 9/2001 | Borchert et al. |
| 6,291,242 | B1 | 9/2001 | Stemmer |
| 6,291,650 | B1 | 9/2001 | Winter et al. |
| 6,297,053 | B1 | 10/2001 | Stemmer |
| 6,303,344 | B1 | 10/2001 | Patten et al. |
| 6,309,883 | B1 | 10/2001 | Minshull et al. |
| 6,319,713 | B1 | 11/2001 | Patten et al. |
| 6,319,714 | B1 | 11/2001 | Crameri et al. |
| 6,323,030 | B1 | 11/2001 | Stemmer |
| 6,326,204 | B1 | 12/2001 | delCardayre et al. |
| 6,326,206 | B1 | 12/2001 | Bjornvad et al. |
| 6,329,178 | B1 | 12/2001 | Patel et al. |
| 6,335,160 | B1 | 1/2002 | Patten et al. |
| 6,335,179 | B1 | 1/2002 | Short |
| 6,335,198 | B1 | 1/2002 | delCardayre et al. |
| 6,337,186 | B1 | 1/2002 | Krebber |
| 6,344,356 | B1 | 2/2002 | Stemmer |
| 6,352,842 | B1 | 3/2002 | Short et al. |
| 6,352,859 | B1 | 3/2002 | delCardayre et al. |
| 6,355,484 | B1 | 3/2002 | Patten et al. |
| 6,358,709 | B1 | 3/2002 | Short et al. |
| 6,358,712 | B1 | 3/2002 | Jarrell et al. |
| 6,358,740 | B1 | 3/2002 | Patten et al. |
| 6,358,742 | B1 | 3/2002 | Stemmer |
| 6,361,974 | B1 | 3/2002 | Short et al. |
| 6,365,377 | B1 | 4/2002 | Patten et al. |
| 6,365,408 | B1 | 4/2002 | Stemmer |
| 6,368,798 | B1 | 4/2002 | Short |
| 6,368,805 | B1 | 4/2002 | Borchert et al. |
| 6,368,861 | B1 | 4/2002 | Crameri et al. |
| 6,372,497 | B1 | 4/2002 | Stemmer |
| 6,376,246 | B1 | 4/2002 | Crameri et al. |
| 6,379,964 | B1 | 4/2002 | Del Cardayre et al. |
| 6,387,702 | B1 | 5/2002 | Stemmer |
| 6,391,552 | B2 | 5/2002 | Stemmer |
| 6,391,640 | B1 | 5/2002 | Minshull et al. |
| 6,395,547 | B1 | 5/2002 | Stemmer |
| 6,399,383 | B1 | 6/2002 | Apt et al. |
| 6,406,855 | B1 | 6/2002 | Patten et al. |
| 6,406,910 | B1 | 6/2002 | Patten et al. |
| 6,413,745 | B1 | 7/2002 | Patten et al. |
| 6,413,774 | B1 | 7/2002 | Stemmer et al. |
| 6,420,715 | B1 | 7/2002 | Cormack et al. |
| 6,423,542 | B1 | 7/2002 | Crameri et al. |
| 6,426,224 | B1 | 7/2002 | Crameri et al. |
| 6,429,004 | B1 | 8/2002 | Murphy et al. |
| 6,436,675 | B1 | 8/2002 | Welch et al. |
| 6,440,668 | B1 | 8/2002 | Short |
| 6,444,426 | B1 | 9/2002 | Short et al. |
| 6,444,468 | B1 | 9/2002 | Stemmer et al. |
| 6,479,258 | B1 | 11/2002 | Short |
| 6,479,652 | B1 | 11/2002 | Crameri et al. |
| 6,482,647 | B1 | 11/2002 | Stemmer |
| 6,483,011 | B1 | 11/2002 | Stemmer et al. |
| 6,489,145 | B1 | 12/2002 | Short |
| 6,489,146 | B2 | 12/2002 | Stemmer et al. |
| 6,492,107 | B1 | 12/2002 | Kauffman et al. |
| 6,632,610 | B2 | 10/2003 | Thill |
| 6,958,213 | B2 * | 10/2005 | Carlsson et al. ................ 435/6 |
| 6,958,334 | B2 | 10/2005 | Carlsson et al. |
| 7,153,655 | B2 * | 12/2006 | Borrebaeck et al. ............ 435/6 |
| 7,282,334 | B2 * | 10/2007 | Carlsson et al. ................ 435/6 |
| 2001/0006950 | A1 | 7/2001 | Punnonen et al. |
| 2001/0032342 | A1 | 10/2001 | Stemmer et al. |
| 2001/0039014 | A1 | 11/2001 | Bass et al. |
| 2001/0049104 | A1 | 12/2001 | Stemmer et al. |
| 2002/0051976 | A1 | 5/2002 | Patten et al. |
| 2002/0058249 | A1 | 5/2002 | Subramanian et al. |
| 2002/0059659 | A1 | 5/2002 | Stemmer et al. |
| 2003/0148353 | A1 | 8/2003 | Borrebaeck et al. |

FOREIGN PATENT DOCUMENTS

| | | |
|---|---|---|
| EP | 0415731 | 3/1991 |
| EP | 0456304 | 11/1991 |
| EP | 0552266 | 7/1993 |
| EP | 0557897 | 9/1993 |
| EP | 0590689 | 4/1994 |
| EP | 0911396 | 4/1999 |
| GB | 9712512.4 | 6/1997 |
| JP | 2001/57893 A | 3/2001 |
| JP | 2001-197895 A | 7/2004 |
| WO | 86/05803 | 10/1986 |
| WO | 90/07936 | 7/1990 |
| WO | 90/14430 | 11/1990 |
| WO | 91/06570 | 5/1991 |
| WO | 91/07506 | 5/1991 |
| WO | 91/15581 | 10/1991 |
| WO | 91/16427 | 10/1991 |
| WO | 92/01047 | 1/1992 |
| WO | 92/07075 | 4/1992 |
| WO | 92/07575 | 5/1992 |
| WO | 92/15702 | 9/1992 |
| WO | 92/18645 | 10/1992 |
| WO | 93/02191 | 2/1993 |
| WO | 93/06213 | 4/1993 |
| WO | 93/07282 | 4/1993 |
| WO | 93/08278 | 4/1993 |
| WO | 93/12257 | 6/1993 |
| WO | 9311237 | 6/1993 |
| WO | 93/15208 | 8/1993 |
| WO | 93/16192 | 8/1993 |
| WO | 93/19172 | 9/1993 |
| WO | 93/25237 | 12/1993 |
| WO | 94/03596 | 2/1994 |
| WO | 94/09817 | 5/1994 |
| WO | 94/12632 | 6/1994 |
| WO | 94/13804 | 6/1994 |
| WO | 94/24313 | 10/1994 |
| WO | 94/28173 | 12/1994 |
| WO | 95/22625 | 8/1995 |
| WO | 96/05803 | 2/1996 |
| WO | 96/17056 | 6/1996 |
| WO | 96/40750 | 12/1996 |
| WO | 96/40987 | 12/1996 |
| WO | 97/07205 | 2/1997 |
| WO | 97/07206 | 2/1997 |
| WO | 97/08320 | 6/1997 |
| WO | 97/20078 | 6/1997 |
| WO | 97/35957 | 10/1997 |
| WO | 97/35966 | 10/1997 |
| WO | 98/01581 | 1/1998 |
| WO | 98/05765 | 2/1998 |
| WO | 98/13485 | 4/1998 |
| WO | 98/13487 | 4/1998 |
| WO | 98/25965 | 6/1998 |

| WO | 98/27230 | 6/1998 |
| WO | 98/28416 | 7/1998 |
| WO | 98/31837 | 7/1998 |
| WO | 98/32845 | 7/1998 |
| WO | 98/41622 | 9/1998 |
| WO | 98/41623 | 9/1998 |
| WO | 98/41653 | 9/1998 |
| WO | 98/42832 | 10/1998 |
| WO | 98/58080 | 12/1998 |
| WO | 99/21979 | 5/1999 |
| WO | 99/23107 | 5/1999 |
| WO | 99/23236 | 5/1999 |
| WO | 99/33965 | 7/1999 |
| WO | 99/41368 | 8/1999 |
| WO | 99/41369 | 8/1999 |
| WO | 99/41383 | 8/1999 |
| WO | 99/41402 | 8/1999 |
| WO | 99/45110 | 9/1999 |
| WO | 99/57128 | 11/1999 |
| WO | 99/58661 | 11/1999 |
| WO | 99/65927 | 12/1999 |
| WO | 00/04190 | 1/2000 |
| WO | 00/09679 | 2/2000 |
| WO | 00/09727 | 2/2000 |
| WO | 00/12680 | 3/2000 |
| WO | 00/18906 | 4/2000 |
| WO | 00/20573 | 4/2000 |
| WO | 00/28008 | 5/2000 |
| WO | 00/28017 | 5/2000 |
| WO | 00/28018 | 5/2000 |
| WO | 00/34512 | 6/2000 |
| WO | 00/42559 | 7/2000 |
| WO | 00/42560 | 7/2000 |
| WO | 00/42561 | 7/2000 |
| WO | 00/46344 | 8/2000 |
| WO | 00/52155 | 9/2000 |
| WO | 00/53744 | 9/2000 |
| WO | 00/58517 | 10/2000 |
| WO | 00/61731 | 10/2000 |
| WO | 00/61740 | 10/2000 |
| WO | 00/72013 | 11/2000 |
| WO | 00/73433 | 12/2000 |
| WO | 00/77262 | 12/2000 |
| WO | 01/00234 | 1/2001 |
| WO | 01/02865 | 1/2001 |
| WO | 01/04287 | 1/2001 |
| WO | 01/12301 | 2/2001 |
| WO | 01/12791 | 2/2001 |
| WO | 01/23401 | 4/2001 |
| WO | 01/25438 | 4/2001 |
| WO | 01/27306 | 4/2001 |
| WO | 01/32712 | 5/2001 |
| WO | 01/34835 | 5/2001 |
| WO | 01/38504 | 5/2001 |
| WO | 01/38513 | 5/2001 |
| WO | 01/42455 | 6/2001 |
| WO | 01/46476 | 6/2001 |
| WO | 01/51663 | 7/2001 |
| WO | 01/64864 | 9/2001 |
| WO | 01/64912 | 9/2001 |
| WO | 01/68803 | 9/2001 |
| WO | 01/70947 | 9/2001 |
| WO | 01/73000 | 10/2001 |
| WO | 01/75087 | 10/2001 |
| WO | 01/75158 | 10/2001 |
| WO | 01/75767 | 10/2001 |
| WO | 01/96551 | 12/2001 |
| WO | 02/04629 | 1/2002 |
| WO | 02/10358 | 2/2002 |
| WO | 02/10750 | 2/2002 |
| WO | 02/16606 | 2/2002 |
| WO | 02/22663 | 3/2002 |
| WO | 02/29032 | 4/2002 |
| WO | 02/29071 | 4/2002 |
| WO | 02/38757 | 5/2002 |
| WO | 02/48351 | 6/2002 |

OTHER PUBLICATIONS

Lowe G et al., "Oligoneric and biogenetic combinatorial libraries", Nat. Prod. Rep. (1999) 16:641-651.
Marks JF et al., "By-passing immunization human antibodies from V-gene libraries displayed in phage", J. Mol. Biol. (1991) 222:581-597.
Marton A et al., "DNA nicking favors PCR recombination", Nucleic Acids Research (1991) 19(9):2423-2426.
McPherson IJ, "Directed Mutagenesis", Oxford Univ. Press, 1991.
Mello Filho AC et al. "In vivo formation fo single-strand breaks in DNA by hydrogen peroxide is mediated by the haber-weiss reaction", Biochim. Biophys. Acta (1984) 781:56-63.
Merz A et al., "Improving the catalytic activity of a thermophilic enzyme at low temperatures", Biochemistry (2000) 39:880-889.
Molecular Cell Biology, 3.sup.rd Ed., (1995), W.H. Freeman and Company, p. G-16.
Mouret JF et al., "Ionic and radiacal oxidations of DNA by Hydrogen Peroxide", Chem. Biol. Interact. (1991) 77 (2):187-201.
Mullis K et al., "Specific Enzymatic Amplification of DNA In Vitro: the Polymerase Chain Reaction", Spring harbor Symp., Quant. Biol. (1986) 51:263-273.
NCBI database entries (partial) for Homo sapiens insulin, myoglobin, L-selection, rhodopsin kinase and complement component C3 mRNAs.
Near RI, "Gene Conversion of Immunoglobulin Variable Regions in Mutagenesis Cassettes by Replacement PCR Mutagenesis", Biotechniques (1992) 12(1):88-97.
Ness JE et al., "DNA shuffling of subgenomic sequences of subtilisin", Nature Biotechnology (1999) 17:893-896.
Ness JE et al., "Molecular Breeding: the natural approach to protein design", Advances in Protein Chemistry (2001) 55:261-292.
Orum H et al., "Efficient method for constructing comprehensive murine Fab antibody libraries displayed on phage", Nucleic Acids Research (1993) 21(19):4491-4498.
Patten AP et al., "Applications of DNA shuffling to pharmaceuticals and vaccines", Current Opinion in Biotechnology (1997) 8:724-733.
Povirk LF et al., "Oxidized apurinic/apyrimidinic sites formed in DNA by oxidative mutagens", Mutation Research (1989) 214:13-22.
Powell SK et al., "Breeding of retroviruses by DNA shuffling for improved stability and processing yields", Nature Biotechnology (2000) 18:1279-1282.
Prodromou C et al., "Recursive PCR: a novel technique for total gene synthesis", Protein Engineering (1992) 5:827-829.
Punnonen J, "Molecular Breeding of Allergy Vaccines and Antiallergic Cytokines", International Archives of Allergy Immunology (2000) 121:173-182.
Punnonen J et al., "Molecular Breeding by DNA Shuffling", Science & Medicine (2000) 121:38-47.
Rhaese HJ et al., "Chemical analysis of DNA alterations. I. Base liberation and backbone breakage of DNA and oligodeoxyadenylic acid induced by hydrogen peroxide and hydroxylamine", Biochim. Biophys. Acta (1968) 155:476-490.
Sagripanti JL et al., "Site-specific oxidative DNA damage at polyguanosines produce by copper plus hydrogen peroxide", Journal of Biological Chemistry (1989) 264(5):1729-1734.
Saiki RK et al., "Primer-directed enzymatic amplification of DNA with a Thermostable DNA polymerase", Science (1988) 239(4838):487-491.
Sambrook J et al., "Molecular Cloning" (1989) Chapters 16-18.
Shi XB et al., "Rapid PCR construction of a gene containing Lym-1 antibody variable regions", PCR Methods and Applications (1993) 3:46-53.
Shuldiner AR et al., "Hybrid DNA artifact from PCR of closely related target sequences", Nucleic Acids Research (1989) 17(11):4409
Soogn NW et al., "Molecular breeding of virses", Nature Genetics (2000) 25;436-439.

Suzuki DT et al., "An Introduction to Genetic Analysis", 4.sup.th Ed., W.H. Freeman and Company, p. 332, 1989.

Tobin MB et al., "Directed evolution: the 'rational' basis for 'irrational' design", Current Opinion in Structural Biology (2000) 10:421-427.

Weisberg EP et al., "Simultaneous mutagensis of multiple sites: application of the ligase chain reaction using PCR products instead of oligonucleotides", Biotechniques (1993) 15(1):68-70, 72-74, 76.

Whalen RG et al., "DNA shuffling and vaccines", Current Opinions in Molecular therapeutics (2001) 3:31-36.

Zaphiropoulos PG et al., "Non-homologous revombination mediated by Thermus aquaticus DNA polymerase I. Evidence supporting a copy choice mechanism", Nucleic Acids Research (1998) 26(12):2843-2848.

Zoller MJ et al., "New recombinant DNA methodology for protein engineering", Current Opinion in biotech (1992) 3:348-354.

Horton RM et al. (1991), "Recombination and mutagenesis of DNA sequences using PCR", Directed Mutagenesis: A Practical Approach. M.J. McPherson, ed. IRL Press, Oxford, p. 217-247.

Malmborg, A-C., "Molecular libraries," website printout, 2 pages, www.immun.lth.se/texter/project mol-libraries.html (Dec. 8, 2005).

Henriquez, V., et al., "A simple strategy to generate small deletions using Bal31 nuclease," Nuc. Acids Res., 18:6735-6736, (1990).

Horton, R.M., et al., "Gene splicing by overlap extension," Methods in Enzymology, 317:270-279, (1993).

Brown, T.A., ed., Molecular Biology LabFax I: Recombinant DNA, Academic Press, San Diego, 128-129, (1998).

Ostermeier, M., et al., "Combinatorial protein engineering by incremenatl truncation," Proc. Natl. Acad. Sci. USA, 96:3562-3567, (1999).

Sharrocks, A., et al., "A rapid method for Bal31 deletion analysis," Nuc. Acids Res., 15:8564, (1987), (ABSTRACT).

Gibbs, M.D., et al., "Degenerate oligonucleotide gene shuffling (DOGS): a method for enhancing the frequency of recombination with family shuffling," Gene, 271:13-20 (2001).

Joern, J.M., et al., "Analysis of Shuffled Gene Libraries," J. Mol. Biol., 316:643-656, (2002).

Kong, X., et al., "Directed Evolution of alpha-Aspartyl Dipeptidase from *Salmonella typhimurium*," Biochemical and Biophysical Research Commun., 289:137-142, (2001).

Lodish, H., et al., "Molecular Cell Biology (Third Edition)," p. G-16, Scientific American Books, (1995).

Lutz, S., et al., "Rapid generation of incremental truncation libraries for protein engineering using alpha-phosphothioate nulceotides," Nucleic Acids Res., 29:E16, (2001).

Ostermeier, M., et al., "Combinatorial protein engineering by incremental truncation," Proc. Natl. Acad. Sci., 96:3562-3567, (1999).

Pelletier, J.N., "A Rachitt for our toolbox: A new twist on DNA shuffling increases recombination frequency and expands access to sequnce space, facilitating the engineering of new protein activities," Nat. Biotechnol., 19:314-315, (2001).

Perlak, F.J., "Single step large scale site-directed in vitro mutagenesis using multipe oligonucleotides," Nucleic Acids Res., 18(24):7457-7458, (1990).

Purves, W.K., et al., Link: The Science of Biology (third ed.), (ISBN 0-7167-2276-3), 55-56, (1992).

Walker, P.M.B., "Chambers Dictionary of Science and Technology," (ISBN 0 550 14110 3), 995, (1999).

http://www.alligatorbioscience.com, (illustration of 04's FIND technology).

Jansen, Ruud and Fred D. Ledley, "Disruption of phase during PCR amplification and cloning of heterozygous target sequences." Nucleic Acids Research, 18(17): 5153-5156 (1990).

Paabo, Svante, et al., "DNA Damage Promotes Jumping between Templates during Enzymatic Amplification." The Journal of Biological Chemistry, 265(8): 4718-4721 (1990).

Lewis, Alan P. and J. Scott Crowe, "Immunoglobin complementarity-determining region grafting by recombinant polymerase chain reaction to generate humanised monoclonal antibodies." Gene, 101: 297-302 (1991).

Goloubinoff, Pierre, et al., "Evolution of maize inferred from sequence diversity of an Adh2 gene segment from archaeological specimens." Proc. Natl. Acad. Sci., 90: 1997-2001 (1993).

Vallette, Francois, et al., "Construction of mutant and chimeric genes using the polymerase chain reaction." Nucleic Acids Research, 17(2): 723-733 (1988).

Sarkar, Gobinda and Steve S. Sommer, "The 'Megaprimer' Method of Site-Directed Mutagenesis." BioTechniques, 8 (4): 404-407 (1990).

Higuchi, Russell, et al., "A general method of in vitro preparation and specific mutagenesis of DNA fragments: study of protein and DNA interactions." Nucleic Acids Research, 16: 7351-7367 (1988).

Innis, Michael A., et al., "PCR Protocols a Guide to Methods and Applications." Academic Press, Inc. (1990).

Higuchi, Russel, "Recombinant PCR." (Chapter 22) in PCR Protocols: A Guide to Methods and Applications. Academic Press, Inc. (1990).

Frohman, Michael A. and Gail R. Martin, "Detection of Homologous Recombinants." (Chapter 28) in PCR Protocols: A Guide to Methods and Applications. Academic Press, Inc. (1990).

Marks, James D., et al., "By-passing Immunization: Human Antibodies from V-gene Libraries Displayed on Phage." J. Mol. Biol., 222: 581-597 (1991).

Nassal, Michael and Andrea Rieger, "PCR-based site-directed mutagenesis using primers with mismatched 3'-ends." Nucleic Acids Research, 18(10): 3077-3078 (1990).

Landt, Olfert, et al., "A general method for rapid site-directed mutagenesis using the polymerase chain reaction." Gene, 96: 125-128 (1990). cited by other.

Berger, Shelby L., et al., "Phoenix Mutagenesis: One-Step Reassembly of Multiply Cleaved Plasmids with Mixtures of Mutant and Wild-Type Fragments." Analytical Biochemistry, 214: 571-579 (1993).

Yon, Jeff and Mike Fried, "Precise gene fusion by PCR." Nucleic Acids Research, 17(12): 4895 (1989).

Horton, Robert M., et al., "Gene Splicing by Overlap Extension: Tailor-Made Genes Using the Polymersase Chain Reaction." BioTechniques, 8(5): 528-535 (1990).

Horton, Robert M., et al., "Gene Splicing by Overlap Extension." Methods in Enzymology, 217: 270-279 (1993).

Smith, Kelly D., et al., "Unwanted Mutations in PCR Mutagenesis: Avoiding the Predictable." PCR Methods and Applications, 2: 253-257 (1993).

Brakenhoff, Ruud H., et al., "Chimeric cDNA clones: a novel PCR artifact." Nucleic Acids Research, 19(8): 1949 (1991).

Horton, Robert M., et al., "Engineering hybrid genes without the use of restriction enzymes: gene splicing by overlap extension." Gene, 77: 61-68 (1989).

Marton, Attila, et al., "DNA nicking favors PCR recombination." Nucleic Acids Research, 19(9):2423-2426 (1991).

Ho, Steffan N., et al., "Site-directed mutagenesis by overlap extension using the polymerase chain reaction." Gene, 77:51-59 (1989).

Arnold FH, "Combinatorial and computational challenges for biocatalyst design", Nature (2001) 409:253-257.

Balint RF et al., "Antibody engineering by parsimonious mutagenesis", Gene (1993) 137(1) :109-118.

Beaudry AA et al., "Directed evolution of an RNA enzyme", Science (1992) 257:635-641.

Berger SL et al., "Phoenix Mutagenesis: One-Step Reassembly of Multiply Cleaved Plasmids with Mixtures of Mutant and Wild-Type Fragments", Analytical Biochemistry (1993) 214:571-579.

Berkhout B et al., "In vivo selection of randomly mutated retroviral genomes", Nucleic Acids Research (1993) 21 (22):5020-5023.

Blakely WF et al., "Radiation-induced binding of DNA from irradiated mammalian cells to hydroxyapatite columns", Radiant Research (1990) 121(3):338-343.

Bourgaux P et a., "Preferred crossover sites on polyomavirus DNA", Journal of Virology (1990) 64(5):2327-2336.

Casorati G et al., "The T cell receptor alpha beta V-J shuffling shows lack of autonomy between the combining site and the constant domain of the receptor chains", Eur. J. Immuno (1993) 23:586-589.

Chambers Dictionary of Science and Technology (1999), p. 995.

Clackson T et al., "Making antibody fragments using phage display libraries", Nature (1991) 352:624-628.

Crameri A, "Improved green fluorescent protein by molecular evolution using DNA shuffling", Nature Biotechnology (1996) 14:315-319.

Daugherty B et al., "Polymerase chain reaction facilitates the cloning, CDR-grafting, and rapid expression of a murine monoclonal antibody directed against the CD18 component of leukocyte integrins", Nucleic Acids Research (1991) 19 (9):2471-2476.

Demple B et al., "5,6-Saturated thymine lesions in DNA: production by ultraviolet light or hydrogen peroxide", Nucleic Acids Research (1982) 10(12):3781-3789.

Dillon PJ et al., "A rapid method for the construction of synthetic genes using the polymerase chain reaction", BioTechniques (1990), 9(3):298-300.

Dimmock NJ et al., "Introduction to Modern Virology", 3rd Ed., Blackwell Scientific Publications, 1987.

Feinberg AP et al., "A technique for radiolabeling DNA restriction endonuclease fragments to high specific activity", Analytical Biochemistry (1983) 132:6-13.

Frappier D et al., "Alternative Homologous and Nonhomologous Products arising from Intramolecular Recombination", journal of Virology (1990) 64(10):5058-5065.

Perlak FJ, "Single step large scale site-directed in vitro mutagenesis using multiple oligonucleotides", Nucleic Acids Research (1990) 18(24):7457-7458.

Hall BG, "toward an understanding of evolutionary potential", FEMS Microbiology Letter (1999) 178:1-6.

Horton RM et al. "Gene splicing by overlap extension: tailor-made genes using the polymerase chain reaction", BioTechniques (1990) 8(5):528-535.

Horton RM et al., "Gene splicing by overlap extension", Methods Enzymol (1993) 217:270-279.

Judo MSB et al. "Stimulation and suppression of PCR-mediated recombination", Nucleic Acids Research (1998) 26 (7):1819-1825.

Kauffman S et al., "Thinking combinatorially", Current Opinion in Chemical Biology (1999) 3:256-259.

Kaushansky K et al., "Structure-function relationships of interleukin-3. An analysis based on the function and binding characteristics of a series of interspecies chimera of gibbon and murine interleukin-3", J Clin Invest. (1992) 90 (5):1879-1888.

Krishanan BR et al., "Direct and crossover PCR amplification to facilitate Tn5supF-based sequencing of .lamda. phage clones", Nucleic acids Research (1991) 19(22):6177-6182.

Lassner M et al., "Directed molecular evolution in plant improvement", Current Opinion in Plant Biology (2001) 4:152-156.

Life: The Science of Biology, 3rd Ed. (1992), Sinauer Associates, p. 55.

Lewin B, "Genes III" (1987), p. 722.

Crameri, Andreas and Willem P. C. Stemmer, "Combinatorial Multiple Cassette Mutagenesis Creates All the Permutations of Mutant and Wild-Type Sequences." BioTechniques, vol. 18, No. 2: 194-196 (1995).

Crameri, Andreas, et al., "DNA shuffling of a family of genes from diverse species accelerates directed evolution." Nature, 391: 288-291 (1998).

Crameri, Andreas, et al., "Molecular evolution of an arsenate detoxification pathway by DNA shuffling." Nature Biotechnology, 15: 436-438 (1997).

Dower, William J., et al., "High efficiency transformation of E. coli by high voltage electroporation." Nucleic Acids Research, vol. 16, No. 13: 6127-6145 (1988).

Eckstein, Fritz. "Exogenous application of ribozymes for inhibiting gene expression." Ciba Foundation Symposium, 207-217 (1997).

Ernst, Wolfgang, et al., "Baculovirus surface display: construction and screening of a eukaryotic epitope library." Nucleic Acids Research, vol. 26, No. 7: 1718-1723 (1998).

Fisch, Igor, et al., "A strategy of exon shuffling for making large peptide repertoires displayed on filamentous bacteriophage." Proc. Natl. Acad. Sci., 93: 7761-7766 (1996).

Grabherr, R., et al., "Expression of Foreign Proteins on the Surface of Autographa californica Nuclear Polyhedrosis Virus." BioTechniques, 22: 730-735 (1997).

Granziero, Luisa, et al., "Baculovirus cDNA libraries for expression cloning of genes encoding cell-surface antigens." Journal of Immunological Methods, 203: 131-139 (1997).

Griffiths, Andrew D., et al., "Isolation of high affinity human antibodies directly from large synthetic repertoires." Journal of Embo., 13(14): 3245-3260 (1994).

Kikuchi, Miho, et al., "An effective family shuffling method using single-stranded DNA." Gene, 243: 133-137 (2000).

Kim, Yong-Sung, et al., "Bacterial Cell Surface Display of an Enzyme Library for Selective Screening of Improved Cellulase Variants." Applied and Environmental Microbiology, vol. 66, No. 2: 788-793 (2000).

Kuipers, Oscar P., et al., "Improved site-directed mutagenesis method using PCR." Nucleic Acids Research, vol. 19, No. 16: 4558 (1991).

Larrick, James W., et al., "Rapid cloning of rearranged immunoglobulin genes from human hybridoma cells using mixed primers and the polymerase chain reaction." Biochemical and Biophysical Research Communications, vol. 160, No. 3: 1250-1256 (1989).

Leung, David W., et al., "A method for random mutagenesis of a defined DNA segment using a modified polymerase chain reaction." Technique-A Journal of Methods in Cell and Molecular Biology, vol. 1, No. 1: 11-15 (1989).

Hanahan, Douglas., "Studies on Transformation of Echerichia coli with Plasmids." J. Mol. Biol., 166: 557-580 (1983).

Higuchi, Kazuo, et al., "Cell display library for gene cloning of variable regions of human antibodies to hepatitis B surface antigen." Journal of Immunological Methods, 202: 193-204 (1997).

Huse, William D., et al., "Generation of Large Combinatorial Library of the Immunoglobulin Repertoire in Phage Lambda." Science, 246: 1275-1281 (1989).

Mottershead, David, et al., "Baculoviral Display of the Green Fluorescent Protein and Rubella Virus Envelope Proteins." Biochemical and Biophysical Research Communications, 238: 717-722 (1997).

McCafferty, John, et al., "Phage antibodies: filamentous phage displaying antibody variable domains." Nature, 348: 552-554 (1990).

Marks, James D., et al., "By-Passing Immunization: Building High Affinity Human Antibodies by Chain Shuffling." Bio/ Technology, 10: 779-783 (1992).

Lu, Tao and Horace B. Gray Jr., "Kinetics and mechanism of BAL 31 nuclease action on small substrates and single-stranded DNA." Biochimica et Biophysica Acta, 1251: 125-138 (1995).

Ostermeier, Marc, et al., "A combinatorial approach to hybrid enzymes independent of DNA homology." Nature Biotechnology, 17: 1205-1209 (1999).

Parmley, Stephen F. and George P. Smith, "Antibody-selectable filamentous fd phage vectors: affinity purification of target genes." Gene, 73: 305-318 (1988).

Schier, Robert, et al., "Isolation of Picomolar Affinity Anti-c-erbB-2 Single-chain Fv by Molecular Evolution of the Complementarity Determining Regions in the Center of the Antibody Binding Site." J. Mol. Biol., 263: 551-567 (1996).

Schmidt, E. R., "Exonuclease digestion of chromosomes for in situ hybridization." Nucleic Acids Res., 16(21): 10381 (1988).

Sock, Elisabeth, et al., "DNA Replication of Human Polyomavirus JC is Stimulated by NF-I in Vivo." Virology, 182: 298-308 (1991).

Stemmer, Willem P. C., "Rapid evolution of a protein In Vitro by DNA shuffling." Nature, 370: 389-391 (1994).

Stemmer, Willem P. C., "DNA shuffling by random fragmentation and reassembly: In Vitro recombination for molecular evolution." Proc. Natl. Acad. Sci., 91: 10747-10751 (1994).

Vaish, Narendra K., et al., "In vitro selection of purine nucleotide-specific hammerhead-like ribozyme." Proc. Natl. Acad. Sci., 95: 2158-2162 (1998).

Warren, Mark S., et al., "A Rapid Screen of Active Site Mutants in Glycinamide Ribonucleotide Transformylase." Biochemistry, 35: 8855-8862 (1996).

Yang, Wei-Ping, et al., "CDR Walking Mutagenesis for the Affinity Maturation of a Potent Human Anti-HIV-1 Antibody into the Picomolar Range." J. Mol. Biol., 254: 392-403 (1995).

Zhang, Ji-Hu, et al., "Directed evolution of a fucosidase from a galactosidase by DNA shuffling and screening." Proc. Natl. Acad. Sci., 94: 4504-4509 (1997).

Paabo, Svante, "Amplifying Ancient DNA." (Chapter 20) in PCR Protocols: A Guide to Methods and Applications. Academic Press, Inc. (1990).

Frank, Ronald, et al., "Simultaneous Synthesis and Biological Applications of DNA Fragements: An Efficient and Complete Methodology." Methods in Enzymology, 154: 221-249 (1987).

Deng, Su-jun, et al., "Simultaneous randomization of antibody CDRs by a synthetic ligase chain reaction strategy." Nucleic Acids Research, vol. 21, No. 18: 4418-4419 (1993).

Meyerhans, Andreas, et al., "DNA recombination during PCR." Nucleic Acids Research, 18(7): 1687-1691 (1990).

Yolov, A. A. and Z. A. Shabarov, "Constructing DNA by polymerase recombination." Nucleic Acids Research, vol. 18, No. 3: 3983-3986 (1990).

Klug, Jorg, et al., "Creating chimeric molecules by PCR directed homologous DNA recombination." Nucleic Acids Research, vol. 19, No. 10: 2793 (1991).

Saiki, Randall K., et al., "Primer-Directed Enzymatic Amplification of DNA with a Thermostable DNA Polymerase." Science, 239: 487-491 (1988).

Daugherty, Bruce L., et al., "Polymerase chain reaction facilities the cloning, CDR-grafting, and rapid expression of a murine monoclonal antibody directed against the CD18 component of leukocyte integrins." Nucleic Acids Research, vol. 19, No. 9: 2471-2476 (1991).

Krishnan, B. Rajendra, et al., "Direct and crossover PCR amplification to facilitate Tn5supF- based sequencing of . lamda. phage clones." Nucleic Acids Research, vol. 19, No. 22: 6177-6182 (1991).

Majumder, Kamud, "Ligation-free gene synthesis by PCR: synthesis and mutagenesis at multiple loci of a chimeric gene encoding OmpA signal peptide and hirudin." Gene, 110: 89-94 (1992).

Heda, Ghanshyam D., et al., "A simple in vitro site directed mutagenesis of concatamerized cDNA by inverse polymerase chain reaction." Nucleic Acids Research, vol. 20, No. 19: 5241-5242 (1992).

Osuna, Joel, et al., "Combinatorial mutagenesis of three major groove-contacting residues of EcoRI: single and double amino acid replacements retaining methyltransferase-sensitive activities." Gene, 106: 7-12 (1991).

Jones, Douglas H. and Stanley C. Winistorfer, "Recombinant Circle PCR and Recombination PCR for Site-Specific Mutagenesis Without PCR Product Purification." BioTechniques, vol. 12, No. 4: 528-534 (1992).

Osuna, Joel, et al., "Microbial Systems and Directed Evolution of Protein Activities." Critical Reviews in Microbiology, 20(2): 107-116 (1994).

Shuldiner, Alan R., et al., "Hybrid DNA artifact from PCR of closely related target sequences." Nucleic Acids Research, vol. 17, No. 11: 4409 (1989).

Gram, Hermann, et al., "In vitro selection and affinity maturation of antibodies from a naive combinatorial immunoglobulin library." Proc. Natl. Acad. Sci., 89: 3576-3580 (1992).

Paabo, Svante, et al., "Ancient DNA and the Polymerase Chain Reaction." The Journal of Biological Chemistry, 264 (17): 9709-9712 (1989).

Kikuchi et al. Novel family shuffling methods for the in vitro evolution of enzymes. Gene, vol. 236, pp. 159-167, 1999.

Berger, et al., "Expanding the Potential of Restriction Endonucleases: Use of Hapaxoterministic Enzymes", Anal. Biochem. 222:1-8, (1994).

Cadwell, et al., "Randomization of Genes by PCR Mutagenesis", PCT Methods Appl., 2:28-33, (1992).

Cadwell, et al., "Mutagenic PCR", PCT Methods Appl., 3:S136-140, (1994).

Casson & Manser, "Evaluationof Loss and Change of Specificity Resulting from Random Mutagenesis of an Antibody V.sub.H Region", J. Immunol. 155: 5647-5654 (1995).

Chalfie, et al., "Green Florescent Protein as a Marker for Gene Expression", Science 263: 802-805 (1994).

Chen, et al., "Tuning the activity of an enzyme for unusual environments: Sequential random mutagenesis of subtilisin E for catalysis in dimethylformamide", Proc. Natl. Acad. Sci. USA 90: 5618-5622.

Crameri, et al., "DNA shuffling of a family of genes from diverse species accelerates directed evolution", Nature, 391: 288-291 (1998).

Deng, et al., "Simultaneous randomization of antibody CDRs by a synthetic ligase chain reaction strategy", Nucl. Acid Res. 21: 4418-4419, (1993).

Engberg, et al., "Phage-Display Libraries of Murine and Human Antibody Fab Fragments", Molecular Biotechnology 6: 287-310, (1996).

Giver, et al., "Directed evolution of a thermostable esterase", Proc. Natl. Acad. Sci USA 95: 12809-12813, (1998).

Gram, et al., "In vitro selection and affinity maturation of antibodies from a naive combinatorial immunoglobuling library", Proc. Natl. Acad. Sci. USA 89: 3576-3580, (1992).

Hansson, et al., "Evolution of Differential Substrate Specificities in Mu Class Glutathione Transferases Probed by DNA Shuffling", J. Mol. Biol. 287: 265-276, (1999).

Henke & Bornscheuer, "Directed Evolution of an Esterase from *Pseudomonas fluorescens*. Random Mutagenesis by Error-Prone PCR or a Mutator Strain and Identification of Mutants Showing Enhanced Enantioselectivity by a Resorufin-Based Fluorescence Assay", Biol. Chem., 380: 1029-1033, (1999).

Ho, et al., "Site-directed mutagenesis by overlap extension using the polymerase chain reaction", Gene 77: 51-59, (1989).

Hoogenboom, et al., "By-passing Immunisation: Human Antibodies from Synthetic Repertoires of Germline V.sub.H Gene Segments Rearranged in Vitro", J. Mol. Biol. 227: 391-388, (1992).

Horton, et al., "Engineering hybrid genes without the use of restriction enzymes: gene splicing by overlap extension", Gene, 77: 61-68, (1989).

Jansen, et al., "Disruption of phase during PCR amplification and cloning heterozygous target sequences", NAR, 18: 5153-5156, (1990).

Kobayashi, et al., "Analysis of Assembly of Synthetic Antibody Fragments: Expression of Functional scFv with Predefined Specificity", Biotechniques, 23: 500-503, (1997).

Kwekkeboom, et al., "CD40 plays an essential role in the activation of human B cells by murine EL4B5 cells", Immunol. 79: 439-444, (1993).

Lewin, "Genes IV", p. 272, Oxford University Press, (1990).

Lewis & Crowe, "Immunoglobulin complementary-determining region grafting by recombinant polymerase chain reaction to generate humanised monoclonal antibodies", Gene 101: 297-302 (1991).

Liu, et al., "Replacement and deletion mutations in the catalytic domain and belt region of *Aspergillus awamori* glucoamylase to enhance thermostability", Protein Eng. 13: 655-659 (2000).

Luqmani & Lymboura, "Subtraction Hybridization Cloning of RNA Amplified From Different Cell Populations Microdissected From Cryostat Tissue Sections", Anal. Biochem., 222: 102-109, (1994).

May, et al., "Inverting enantioselectivity by directed evolution of hydantoinase for improved production of L-methionine", Nat. Biotechnol. 18: 317-320, (2000).

Meyerhans, et al., "DNA recombination during PCR", Nucl. Acid Res., 18: 1687-91, (1990).

Moore, et al., "Directed evolution of a para-nitrobenzyl esterase for aqueous-organic solvents", Nature Biotechnology, 14: 458-467 (1996).

Orlandi, et al., "Cloning immunoglobulin variable domains for expression by the polymerase chain reaction", Proc. Natl. Acad. Sci. USA, 86: 3833-3837 (1989).

Paabo, et al., "Ancient DNA and the Polymerase Chain Reaction", J. Biol. Chem., 264: 9709-9712, (1989).

Paabo, et al., "DNA Damage Promotes Jumping between Templates during Enzymatic Amplification", J. Biol. Chem., 265: 4718-4721, (1990).

Prickett, et al., "A Calcium-Dependent Antibody for Identification and Purification of Recombinant Proteins", BioTechniques, 7: 580-589, (1989).

Roberts, et al., "Generation of an antibody with enhanced affinity and specificity for its antigen by protein engineering", Nature, 328: 731-734, (1987).

Schmidt-Dannert, et al., "Molecular breeding of carotenoid biosynthetic pathways", Nat. Biotechnol., 18: 750-753, (2000).

Shyur, et al., "Site-directed Mutagenesis of Residues at Subunit Interfaces of Procine Fructose- 1,6-bisphosphatase", J. Biol. Chem., 271: 3005-3010, (1996).

Soderlind, et al., "Domain libraries: Synthetic diversity for de novo design of antibody V-regions", Gene, 160: 269-272, (1995).

Song, et al., "Simultaneous Enhancement of Thermostability and Catalytic Activity of Phospholipase A$_1$ by Evolutionary Molecular Engineering", Appl. Environ. Microbiol. 66: 890-894, (2000).

Volkov, et al., "Methods for in Vitro DNA Recombination and Random Chimeragenesis", Methods Enzymol., 328: 447-456 (2000).

Wan, et al., "In vitro evolution of horse heart myoglobin to increase peroxidase activity", Proc. Natl. Acad. Sci. USA, 95: 12825-12831 (1998).

Zhao & Arnold, "Directed evolution converts subtilisin E into a functional equivalent of thermitase", Protein Eng., 12: 47-53, (1999).

Zhao, et al., "Molecular evolution by staggered extension process (StEP) in vitro recombination", Nat. Biotechnol. 16: 258-261 (1998).

Alber, Tom, et al., "Contributions of hydrogen bonds of Thr 157 to the thermodynamic stability of phage T4 lysozyme." Nature, 330: 41-46 (1987).

Arrizubieta, Maria Jesus and Julio Polaina. "Increased Thermal Resistance and Modification of the Catalytic Properties of a .beta.-Glucosidase by Random Mutagenesis and in Vitro Recombination." The Journal of Biological Chemistry, vol. 275, No. 37: 28843-28848 (2000).

Barbas, III, Carlos F., et al., "Assembly of combinatorial antibody libraries on phage surfaces: The gene III site." Proc. Natl. Acad. Sci., 88: 7978-7982 (1991).

Barbas, III, Carlos F., et al., "Semisynthetic combinatorial antibody libraries: A chemical solution to the diversity problem." Proc. Natl. Acad. Sci., 89: 4457-4461 (1992).

Boder, Eric T. and K. Dane Wittrup, "Yeast surface display for screening combinatorial polypeptide libraries." Nature Biotechnology, 15: 553-557 (1997).

Boublik, Yvan, et al., "Eukaryotic Virus Display: Engineering the Major Surface Glycoprotein of the Autographa californica Nuclear Polyhedrosis Virus (AcNPV) for the Presentation of Foreign Proteins on the Virus Surface." Bio/technology, 13: 1079-1084 (1995).

"DNA and RNA Modifying Enzymes." (Chapter 5) in Molecular Biology LabFax, ed. T. A. Brown. BIOS Scientific Publishers, Ltd. and Blackwell Scientific Publishers Ltd. (1991).

Buchholz, Christian J., et al., "In vivo selection of protease cleavage sites from retrovirus display libraries."0 Nature Biotechnology, 16: 951-954 (1998).

Chang, Chia-Chun J., et al., "Evolution of a cytokine using DNA family shuffling." Nature Biotechnology, 17: 793-797 (1999).

Christians, Fred C., et al., "Directed evolution of thymidine kinase for AZT phosphorylation using DNA family shuffling." Nature Biotechnology, 17: 259-264 (1999).

* cited by examiner

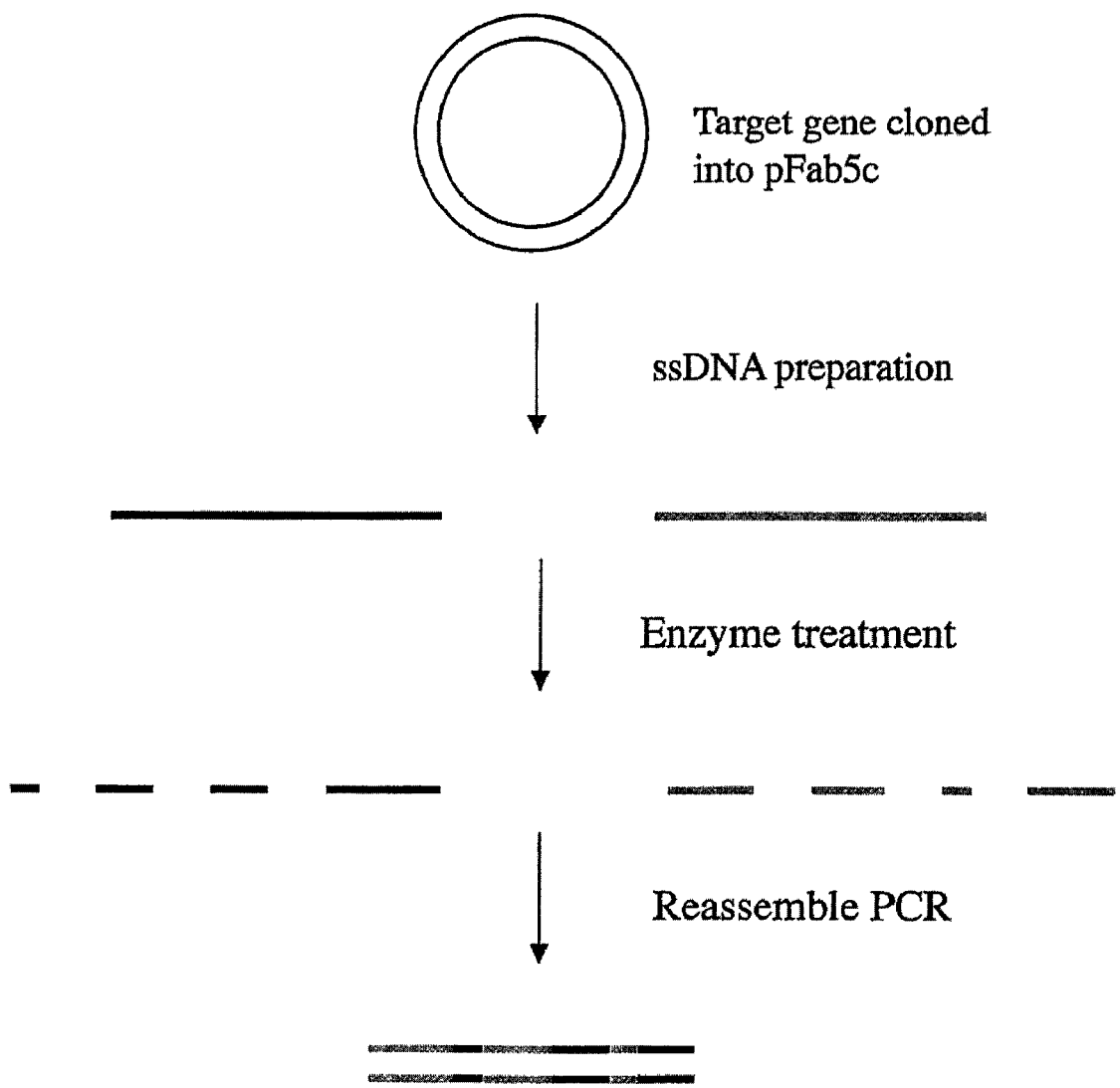
Figure 1. The principle of the method from template molecule to improved molecule.

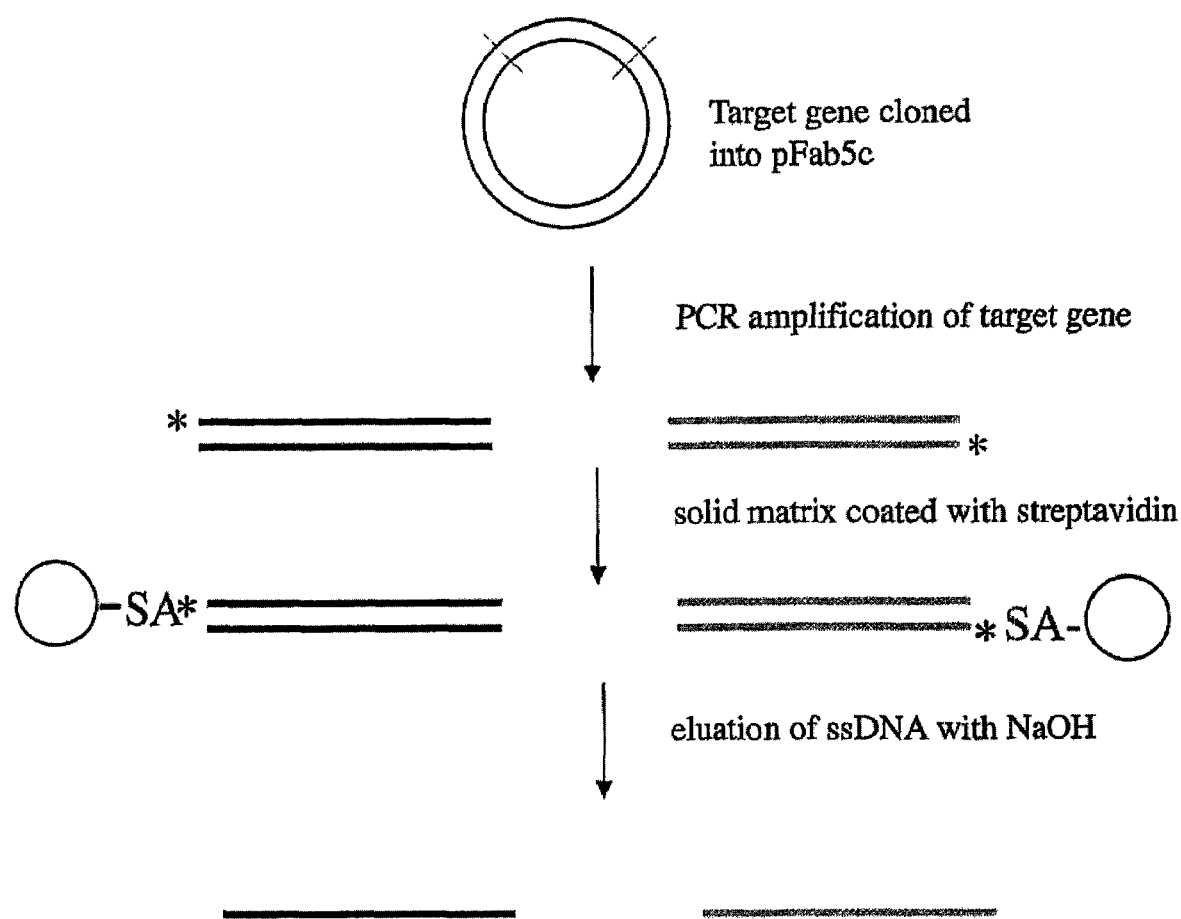
Figure 2. Preparation of single stranded DNA using biotinylated primers.

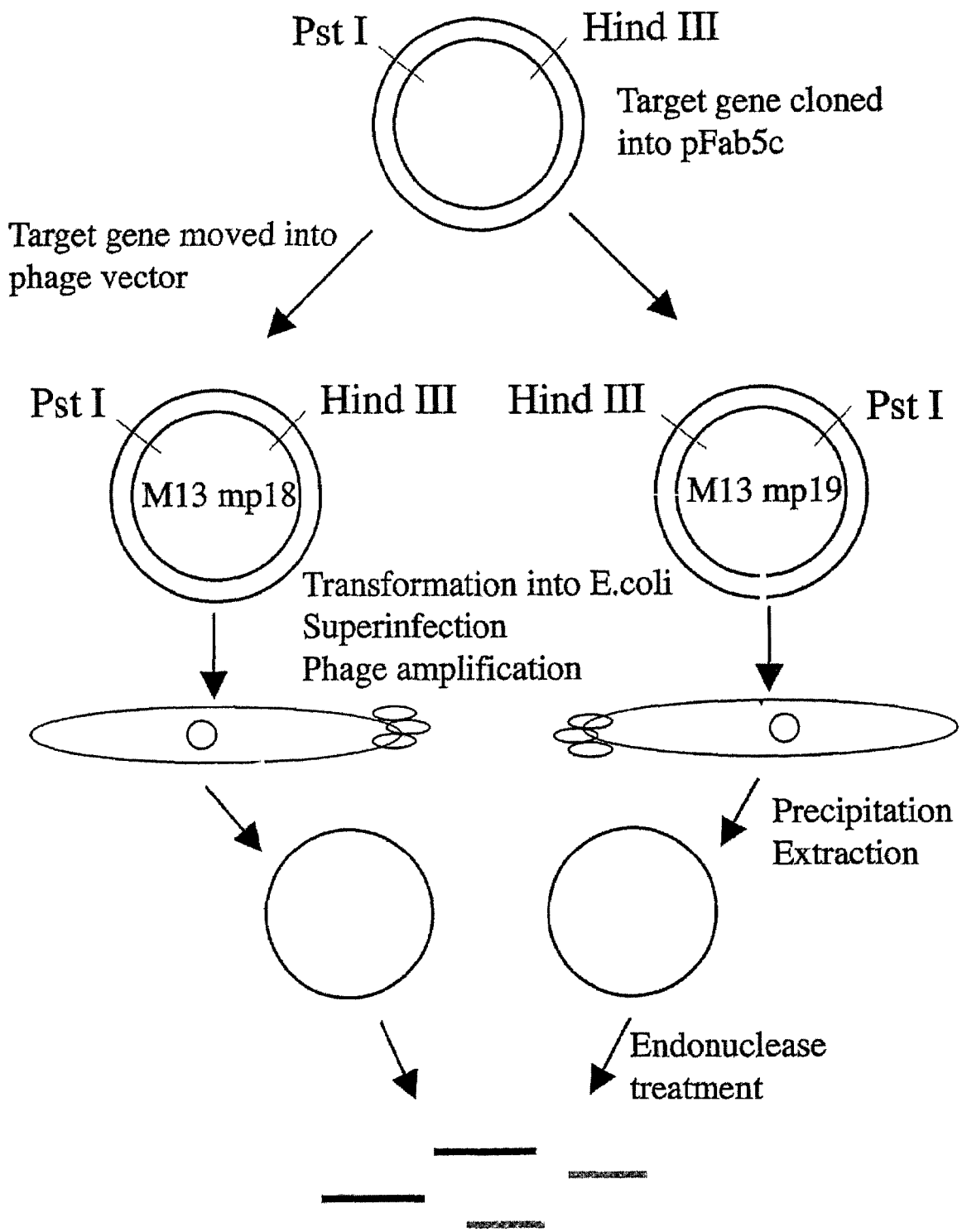
Figure 3. Preparation of single stranded DNA using phage.

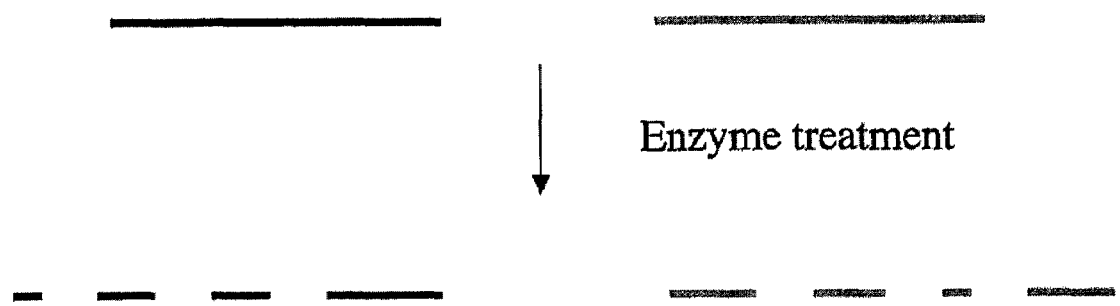
Figure 4. Generating single stranded DNA fragments using exonuclease treatment.

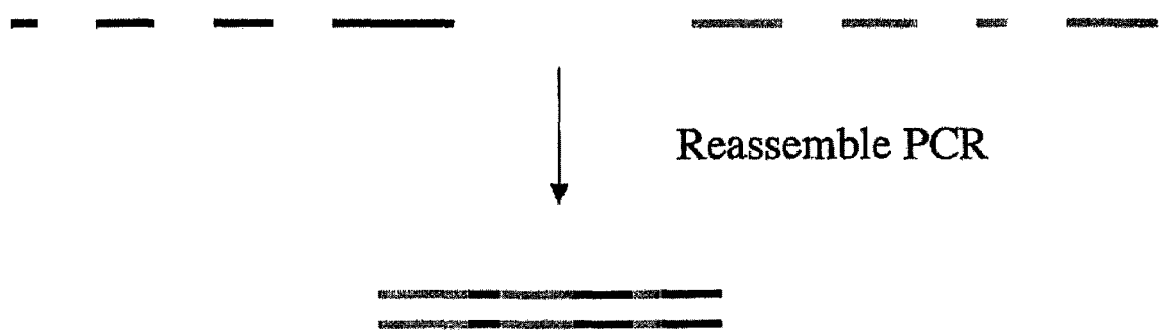
Figure 5. The ssDNA fragments are reassembled by PCR.

SEQUENCE LISTING

<160> NUMBER OF SEQ ID NOS: 2

<210> SEQ ID NO 1
<211> LENGTH: 44
<212> TYPE: DNA

```
<213> ORGANISM: Artificial Sequence
<220> FEATURE:
<223> OTHER INFORMATION: primer

<400> SEQUENCE: 1
attactcgcg gcccagccgg ccatggccca caggtcaagc tcga          44

<210> SEQ ID NO 2
<211> LENGTH: 35
<212> TYPE: DNA
<213> ORGANISM: Artificial Sequence
<220> FEATURE:
<223> OTHER INFORMATION: primer

<400> SEQUENCE: 2
ttagagcctg cggccgcctt gtcatcgtcg tcctt                    35
```

METHOD FOR IN VITRO MOLECULAR EVOLUTION OF PROTEIN FUNCTION

This application is a continuation application of U.S. patent application Ser. No. 11/185,044 filed Jul. 20, 2005 now U.S. Pat. No. 7,282,334, which is a continuation of U.S. patent application Ser. No. 09/734,801 filed Dec. 12, 2000 now U.S. Pat. No. 6,958,213. The entire disclosure of each of the foregoing applications is incorporated by reference herein.

FIELD OF THE INVENTION

The present invention relates to a method for in vitro molecular evolution of protein function, in particular by shuffling of single stranded DNA segments obtained using a nuclease.

BACKGROUND OF THE INVENTION

Protein function can be modified and improved in vitro by a variety of methods, including site directed mutagenesis (Alber et al., Nature, 5; 330 (6143): 41-46, 1987) combinatorial cloning (Huse et al., Science, 246: 1275-1281, 1989; Marks et al., Biotechnology, 10: 779-783, 1992) and random mutagenesis combined with appropriate selection systems (Barbas et al., PNAS. USA, 89: 4457-4461, 1992).

The method of random mutagenesis together with selection has been used in a number of cases to improve protein function and two different strategies exist. Firstly, randomisation of the entire gene sequence in combination with the selection of a variant (mutant) protein with the desired characteristics, followed by a new round of random mutagenesis and selection. This method can then be repeated until a protein variant is found which is considered optimal (Schier R. et al., J. Mol. Biol. 1996 263 (4): 551-567). Here, the traditional route to introduce mutations is by error prone PCR (Leung et al., Technique, 1: 11-15, 1989) with a mutation rate of approximately 0.7%. Secondly, defined regions of the gene can be mutagenized with degenerate primers, which allows for mutation rates up to 100% (Griffiths et al., EMBO. J, 13: 3245-3260, 1994; Yang et al., J. Mol. Biol. 254: 392-403, 1995). The higher the mutation rate used, the more limited the region of the gene that can be subjected to mutations.

Random mutation has been used extensively in the field of antibody engineering. In vivo formed antibody genes can be cloned in vitro (Larrick et al., Biochem. Biophys. Res. Commun. 160: 1250-1256, 1989) and random combinations of the genes encoding the variable heavy and light genes can be subjected to selection (Marks et al., Biotechnology, 10: 779-783, 1992). Functional antibody fragments selected can be further improved using random mutagenesis and additional rounds of selections (Schier R. et al., J. Mol. Biol. 1996 263 (4): 551-567).

The strategy of random mutagenesis is followed by selection. Variants with interesting characteristics can be selected and the mutated DNA regions from different variants, each with interesting characteristics, are combined into one coding sequence (Yang et al., J. Mol. Biol. 254: 392-403, 1995). This is a multi-step sequential process, and potential synergistic effects of different mutations in different regions can be lost, since they are not subjected to selection in combination. Thus, these two strategies do not include simultaneous mutagenesis of defined regions and selection of a combination of these regions. Another process involves combinatorial pairing of genes which can be used to improve e.g. antibody affinity (Marks et al., Biotechnology, 10: 779-783, 1992). Here, the three CDR-regions in each variable gene are fixed and this technology does not allow for shuffling of individual gene segments in the gene for the variable domain, for example, including the CDR regions, between clones.

The concept of DNA shuffling (Stemmer, Nature 370: 389-391, 1994) utilizes random fragmentation of DNA and assembly of fragments into a functional coding sequence. In this process it is possible to introduce chemically synthesized DNA sequences and in this way target variation to defined places in the gene which DNA sequence is known (Crameri et al., Biotechniques, 18: 194-196, 1995). Stemmer and coworkers developed this in vitro method, which reassemble the normally occurring evolution process of protein in nature. The DNA shuffling generates diversity by recombination, combining useful mutations from individual genes. It has been used successfully for artificial evolution of different proteins, e.g. enzymes and cytokines (Chang et al. Nature Biotech. 17, 793-797, 1999; Zhang et al. Proc. Natl. Acad. Sci. USA 94, 4504-4509, 1997; Christians et al. Nature Biotech. 17, 259-264, 1999). The genes are randomly fragmented using DNase I and then reassembled by recombination with each other. The starting material can be either a single gene (first randomly mutated using error-prone PCR) or naturally occurring homologous sequences so called family shuffling. DNase I hydrolyses DNA preferentially at sites adjacent to pyrimidine nucleotides, therefore it is a suitable choice for random fragmentation of DNA. However, the activity is dependent on Mg or Mn ions, Mg ions restrict the fragment size to 50 bp, while the Mn ions will give fragment sizes less than 50 bp. Therefore, in order to have all possible sizes for recombination the gene in question needs to be treated at least twice with DNase I in the presence of either of the two different ions, followed by removal of these very same ions.

In theory, it is possible to shuffle DNA between any clones. However, if the resulting shuffled gene is to be functional with respect to expression and activity, the clones to be shuffled have preferably to be related or even identical with the exception of a low level of random mutations. DNA shuffling between genetically different clones will generally produce non-functional genes. However, it has been proven by the methodology of ITCHY that interspecies fusion libraries can be created between fragments of the E. coli and human glycinamide ribonucleotide transformylase genes, which have only 50% identity on the DNA level (Ostermeier et al., Nat Biotechnol 17, 1205-9, 1999).

A successful recombination of two different genes requires formation of hetero-duplex molecules. In some cases the family shuffling almost only form homo-duplexes resulting in a low frequency of recombination. This problem has been addressed by using DNase I-digested single-stranded DNA (Kikuchi et al. Gene 243, 133-137, 2000).

Single-stranded DNA can be obtained in essentially two different ways. Firstly, by the use of biotinylated primers in the PCR reactions in combination with e.g. Dynabeads (Dynal, Norway) or AffiniTip Streptavidin Capture Micro-columns (Genosys Biotechnologies Inc., The Woodlands, USA). Secondly, by utilising bacteriophage that are able to pack single-stranded DNA (Viruses and Related Entities in Modern Microbiology, Principles and Applications pp. 171-192, Ed. E. A. Birge, Wm. C. Brown Publishers 1992; Sambrook et al. Molecular Cloning, A laboratory manual 2nd edition. Cold Spring Harbor Laboratory Press, 1989).

Selection of enzymes with altered and improved properties are often based on the actual function of the enzyme. For example increased thermostability of an enzyme can be selected for by incubating transformed colonies at temperatures that cause inactivation of wild type enzyme and improved β-glucosidase activity can be identified by using PNPG as the substrate (Arrizubieta et al J Biol Chem Jun. 27, 2000).

Selection of functional proteins from molecular libraries has been revolutionized by the development of the phage display technology (Parmley et al., Gene, 73: 305-391 1988; McCafferty et al., Nature, 348: 552-554, 1990; Barbas et al., PNAS. USA, 88: 7978-7982, 1991). Here, the phenotype (protein) is directly linked to its corresponding genotype (DNA) and this allows for directly cloning of the genetic material which can then be subjected to further modifications in order to improve protein function. Phage display has been used to clone functional binders from a variety of molecular libraries with up to $10^{11}$ transformants in size (Griffiths et al., EMBO. J. 13: 3245-3260, 1994). Thus, phage display can be used to directly clone functional binders from molecular libraries, and can also be used to improve further the clones originally selected. Other types of viruses that have been used for surface expression of protein libraries and selections thereof are baculovirus (Boublik et al Biotechnol 13: 1079-1084. 1995; Mottershead et al Biochem Biophys Res Com 238:717-722, 1997; Grabherr et al Biotechniques 22: 730-735, 1997) and retrovirus (Buchholz et al Nature Biotechnol 16: 951-954, 1998).

Selection of functional proteins from molecular libraries can also be performed by cell surface display. Also here, the phenotype is directly linked to its corresponding genotype. Bacterial cell surface display has been used for e.g. screening of improved variants of carbozymethyl cellulase (CMCase) (Kim et al Appl Environ Microbiol 66: 788-93, 2000). Other cells that can be used for this purpose are yeast cells (Boder and Wittrup Nat. Biotechnol 15:553-557, 1997), COS cells (Higuchi et al J Immunol Meth 202: 193-204, 1997), and insect cells (Granzerio et al J Immunol Meth 203:131-139, 1997; Ernst et al Nucleic Acids Res 26:1718-1723, 1998).

Random combination of DNA from different mutated clones in combination with selection of desired function is a more efficient way to search through sequence space as compared to sequential selection and combination of selected clones.

This invention seeks to provide improved methods for in vitro protein evolution. In particular, the invention aims to provide more efficient recombination and shuffling methods, which will give rise to more altered molecules and thereby improve the probability of finding molecules with desirable properties.

SUMMARY OF THE INVENTION

According to one aspect of the present invention, there is provided a method for generating a polynucleotide sequence or population of sequences from parent single stranded polynucleotide sequences encoding one or more protein motifs, comprising the steps of
  a) providing single stranded DNA constituting plus and minus strands of parent polynucleotide sequences;
  b) digesting the single stranded polynucleotide sequences with a nuclease other than DNase I to generate populations of single stranded fragments;
  c) contacting said fragments generated from the plus strands with fragments generated from the minus strands and optionally, adding primer sequences that anneal to the 3' and 5' ends of at least one of the parent polynucleotides under annealing conditions;
  d) amplifying the fragments that anneal to each other to generate at least one polynucleotide sequence encoding one or more protein motifs having altered characteristics as compared to the one or more protein motifs encoded by said parent polynucleotides.

Therefore, typically, there is provided a method of combining polynucleotide fragments to generate a polynucleotide sequence or population of sequences of desired characteristics, which method comprises the steps of:

(a) digesting a linear parent single-stranded polynucleotide encoding one or more protein motifs with a nuclease other than DNase I to generate a population of single-stranded fragments of varying lengths;
  (b) assembling a polynucleotide sequence from the sequences derived from step (a).

Preferably the method further comprises the step of (c) expressing the resulting protein encoded by the assembled polynucleotide sequence and d) screening the protein for desired characteristics.

Preferably the nuclease other than DNase I is an exonuclease.

By controlling the reaction time of the nuclease the size of the polynucleotide fragments may be determined. Determining the lengths of the polynucleotide fragments in this way avoids the necessity of having to provide a further step such as purifying the fragments of desired length from a gel.

In order to generate a polynucleotide sequence of desired characteristics the parent polynucleotide encoding one or more protein motifs may be subjected to mutagenesis to create a plurality of differently mutated derivatives thereof. Likewise, a parent polynucleotide may be obtained already encoding a plurality of variant protein motifs of unknown sequence.

Random mutation can be accomplished by any conventional method as described above, but a suitable method is error-prone PCR.

It is preferable to use PCR technology to assemble the single-stranded polynucleotide fragments into a double-stranded polynucleotide sequence.

The polynucleotide sequence is preferably DNA although RNA may be used. For simplicity the term polynucleotide will now be used in the following text in relation to DNA but it will be appreciated that the present invention is applicable to both RNA and DNA.

Preferably, any exonuclease that digests polynucleotide from the 5' prime end to the 3' prime, from the 3' to the 5' end or from both the 3' and the 5' ends may be used. Examples of a suitable exonuclease which may be used in accordance with the present invention include BAL31, T7 gene 6 exonuclease, and Exonuclease VII.

Using BAL31 nuclease in the DNA shuffling process of the invention provides a fast, easy and controllable system. This enzyme can give all sizes of gene fragments and the activity of the enzyme can be easily controlled by stopping the digestion at various time points. BAL 31 is predominately a 3' prime exonuclease that removes mononucleotides from both 3' termini of the two strands of a linear DNA. BAL 31 is also an endonuclease; thus the single-stranded DNA generated by the 3' prime exonuclease activity is degraded by the endonuclease. The 3' prime exonuclease activity of the enzyme works about 20-fold more efficiently than the endonuclease. The enzyme concentrations are therefore important for the obtained DNA fragments. High concentration of enzyme favors blunt-ended DNA whereas at low concentrations the single-stranded DNA termini may be very long. BAL 31 consists of two kinetically distinct forms of the enzyme, a fast (F) and a slow (S) form. The S form is a proteolytic degradation product of the F form. Furthermore, BAL 31 works asynchronously, generating a population of DNA molecules whose termini have been resected to various extents and whose single-stranded tails vary in length. Both forms also act on ssDNA in an exonucleolytic fashion in a highly processive manner. The direction of attack is from the 5' end, in contrast to the mode of digestion of duplex DNA. It has been suggested that the nuclease molecules initially are non-productively bound away from the 5' ends and undergo facilitated diffusion to yield productive (terminally bound) enzyme-substrate complexes (Lu T and Gray jr. HB Biochimica et Biophysica Acta 1995, vol. 1251, p 125-138). The enzyme uses $Ca^{2+}$ as a co-factor which can be bound in complex with EGTA (Ethylene Glycol bis(β-amino ethyl Ether) N,N,N',N'-tetra acetic acid). Linear DNA sequences are digested with BAL31 and the reaction stopped at different time points by the addition of EGTA.

The individual digested fragments are purified, mixed and reassembled with PCR technology. The assembled (reconstituted) gene may then be cloned into an expression vector for expressing the protein. The protein may then be analyzed for improved characteristics.

The method of the present invention provides several advantages over known shuffling techniques.

Further, the method of the present invention produces a set of progressively shortened DNA fragments for each time point a DNA sample is taken from the BAL31 treatment. The DNA samples may be collected and pooled together or, optionally, individual samples may be chosen and used in the method. Thus the present invention allows a selection of what DNA samples are to be used in the recombination system and thereby offers a further degree of control.

The method of the present invention may be carried out on any polynucleotide which codes for a particular product for example any protein having binding or catalytical properties e.g. antibodies or parts of antibodies, enzymes or receptors. Further, any polynucleotide that has a function that may be altered for example catalytical RNA may be shuffled in accordance with the present invention. It is preferable that the parent polynucleotide encoding one or more protein motif is at least 12 nucleotides in length, more preferably at least 20 nucleotides in length, even more preferably more than 50 nucleotides in length. Polynucleotides being at least 100 nucleotides in length or even at least 200 nucleotides in length may be used. Where parent polynucleotides are used that encode large proteins such as enzymes or antibodies, these may be many hundreds or thousands of bases in length. The present invention may be carried out on any size of parent polynucleotide.

The present invention also provides polynucleotide sequences generated by the method described above having desired characteristics. These sequences may be used for generating gene therapy vectors and replication-defective gene therapy constructs or vaccination vectors for DNA-based vaccinations. Further, the polynucleotide sequences may be used as research tools.

The present invention also provides a polynucleotide library of sequences generated by the method described above from which a polynucleotide may be selected which encodes a protein having the desired characteristics. It is preferable that the polynucleotide library is a DNA or cDNA library.

The present inventions also provides proteins such as enzymes, antibodies, and receptors having characteristics different to that of the wild type produced by the method described above. These proteins may be used individually or within a pharmaceutically acceptable carrier as vaccines or medicaments for therapy, for example, as immunogens, antigens or otherwise in obtaining specific antibodies. They may also be used as research tools.

The desired characteristics of a polynucleotide generated by the present invention or a protein encoded by a polynucleotide generated by the present invention may be any variation or alteration in the normal activity of the wild type (parent) polynucleotide or the polypeptide, protein or protein motifs it encodes. For example, it may be desirable to reduce or increase the catalytic activity of an enzyme, or improve or reduce the binding specificity of an antibody. Further, if the protein, or polynucleotide is an immunogen, it may be desirable to reduce or increase its ability to obtain specific antibodies against it. The parent polynucleotide preferably encodes one or more protein motifs. These are defined by regions of polynucleotide sequence, that encode polypeptide sequence having or potentially having characteristic protein function. For example, a protein motif may define a portion of a whole protein, i.e. an epitope or a cleavage site or a catalytic site etc. However, within the scope of the present invention, an expressed protein motif does not have to display activity, or be "correctly" folded.

It may be desirable to modify a protein so as to alter the conformation of certain epitopes, thereby improving its antigenicity and/or reducing cross-reactivity. For example, should such a protein be used as an antigen, the modification may reduce any cross-reaction of raised antibodies with similar proteins.

Although the term "enzyme" is used, this is to be interpreted as also including any polypeptide having enzyme-like activity, i.e. a catalytic function. For example, polypeptides being part of an enzyme may still possess catalytic function. Furthermore, proteins such as interferons and cytokines are included. Likewise, the term "antibody" should be construed as covering any binding substance having a binding domain with the required specificity. This includes antibody fragments, derivatives, functional equivalents and homologues of antibodies, including synthetic molecules and molecules whose shape mimics that of an antibody enabling it to bind an antigen or epitope. Examples of antibody fragments, capable of binding an antigen or other binding partner are Fab fragment consisting of the VL, VH, C1 and CH1 domains, the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

In order to obtain expression of the generated polynucleotide sequence, the sequence may be incorporated in a vector having control sequences operably linked to the polynucleotide sequence to control its expression. The vectors may include other sequences such as promoters or enhancers to drive the expression of the inserted polynucleotide sequence, further polynucleotide sequences so that the protein encoded for by the polynucleotide is produced as a fusion and/or nucleic acid encoding secretion signals so that the protein produced in the host cell is secreted from the cell. The protein encoded for by the polynucleotide sequence can then be obtained by transforming the vectors into host cells in which the vector is functional, culturing the host cells so that the protein is produced and recovering the protein from the host cells or the surrounding medium. Prokaryotic and eukaryotic cells are used for this purpose in the art, including strains of *E. coli*, yeast, and eukaryotic cells such as COS or CHO cells. The choice of host cell can be used to control the properties of the protein expressed in those cells, e.g. controlling where the protein is deposited in the host cells or affecting properties such as its glycosylation.

The protein encoded by the polynucleotide sequence may be expressed by methods well known in the art. Conveniently, expression may be achieved by growing a host cell in culture, containing such a vector, under appropriate conditions which cause or allow expression of the protein.

Systems for cloning and expression of a protein in a variety of different host cells are well known. Suitable host cells include bacteria, eukaryotic cells such as mammalian and yeast, and baculovirus systems. Also, utilising the retrovirus system for cloning and expression is a good alternative, since this virus can be used together with a number of cell types. Mammalian cell lines available in the art for expression of a heterologous polypeptide include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of polynucleotide sequences, for example in preparation of polynucleotide constructs, mutagenesis, sequencing, introduction of DNA into cells and gene expression, and analysis of proteins, are described in detail in Current Protocols in Molecular Biology, Ausubel et al. eds., John Wiley & Sons, 1992.

The system can be used for the creation of DNA libraries comprising variable sequences which can be screened for the desired protein function in a number of ways. Enzyme function can be screened for with methods specific for the actual enzyme function e.g. CMCase activity, β-glucosidase activity and also thermostability. Furthermore, phage display and cell surface display may be used for screening for enzyme function (Crameri A. et al., Nature 1998 15; 391 (6664): 288-291; Zhang J. H. et al., PNAS. USA 1997 94 (9): 4504-4509; Warren M. S. et al., Biochemistry 1996, 9; 35 (27): 8855-8862; Kim et al., Appl Environ Microbiol 66: 788-93, 2000) as well as for altered binding properties of eg. antibodies (Griffith et al., EMBO J. 113:3245-3260, 1994).

A protein provided by the present invention may be used in screening for molecules which affect or modulate its activity or function. Such molecules may be useful in a therapeutic (possibly including prophylactic) context.

The present invention also provides vectors comprising polynucleotide sequences generated by the method described above.

The present inventions also provides compositions comprising either polynucleotide sequences, vectors comprising the polynucleotide sequences or proteins generated by the method described above and a pharmaceutically acceptable carrier or a carrier suitable for research purposes.

The present invention also provides a method comprising, following the identification of the polynucleotide or polypeptide having desired characteristics by the method described above, the manufacture of that polypeptide or polynucleotide in whole or in part, optionally in conjunction with additional polypeptides or polynucleotides.

Following the identification of a polynucleotide or polypeptide having desired characteristics, these can then be manufactured to provide greater numbers by well known techniques such as PCR, cloning and expression within a host cell.

The resulting polypeptides or polynucleotides may be used in the preparation of industrial enzymes, eg. laundry detergent enzymes where an increased activity is preferred at lower temperatures. Alternatively, the manufactured polynucleotide or polypeptide may be used as a research tool, i.e. antibodies may be used in immunoassays, and polynucleotides may be used as hybridization probes or primers. Alternatively, the resulting polypeptides or polynucleotides may be used in the preparation of medicaments for diagnostic use, pharmaceutical use, therapy etc. as discussed as follows.

The polypeptides or polynucleotides generated by the method of the invention and identified as having desirable characteristics can be formulated in pharmaceutical compositions. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

Whether it is a polypeptide, e.g. an antibody or fragment thereof, an enzyme, a polynucleotide or nucleic acid molecule, identified following generation by the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, e.g. in a viral vector (a variant of the VDEPT technique i.e. the activating agent, e.g. an enzyme, is produced in a vector by expression from encoding DNA in a viral vector). The vector could be targeted to the specific cells to be treated, or it could contain regulatory elements which are switched on more or less selectively by the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. an enzyme, in a vector by expression from encoding DNA in a viral vector (see for example, EP-A-415731 and WO 90/07936).

A composition may be administered alone or in combination with other treatments, either simultaneously or sequentially dependent upon the condition to be treated.

As a further alternative, the polynucleotide identified as having desirable characteristics following generation by the method of the present invention could be used in a method of gene therapy, to treat a patient who is unable to synthesize the active polypeptide encoded by the polynucleotide or unable to synthesize it at the normal level, thereby providing the effect provided by the corresponding wild-type protein.

Vectors such as viral vectors have been used in the prior art to introduce polynucleotides into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted tumour cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpes viruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

As mentioned above, the aim of gene therapy using nucleic acid encoding a polypeptide, or an active portion thereof, is to increase the amount of the expression product of the nucleic acid in cells in which the level of the wild-type polypeptide is absent or present only at reduced levels. Such treatment may be therapeutic in the treatment of cells which are already cancerous or prophylactic in the treatment of individuals known through screening to have a susceptibility allele and hence a predisposition to, for example, cancer.

The present invention also provides a kit for generating a polynucleotide sequence or population of sequences of desired characteristics comprising reagents for ssDNA preparation, an exonuclease and components for carrying out a PCR technique, for example, thermostable DNA (nucleotides) and a stopping device, for example, EGTA.

As outlined above the present invention conveniently provides for the creation of mutated enzyme gene sequences and their random combination to functional enzymes having desirable characteristics. As an example of this aspect of the invention, the enzyme genes are mutated by error prone PCR which results in a mutation rate of approximately 0.7%. The resulting pool of mutated enzyme genes are then digested with an exonuclease, preferably BAL31, and the reaction inhibited by the addition of EGTA at different time points, resulting in a set of DNA fragments of different sizes. These may then be subjected to PCR based reassembly as described above. The resulting reassembled DNA fragments are then cloned and a gene library constructed. Clones may then be selected from this library and sequenced.

A further application of this technology is the generation of a population of variable DNA sequences which can be used for further selections and analyses. Besides encoding larger proteins, e.g. antibody fragments and enzymes, the DNA may encode peptides where the molecules functional characteristics can be used for the design of different selection systems. Selection of recombined DNA sequences encoding peptides has previously been described (Fisch et al., PNAS. USA 1996 Jul. 23; 93 (15): 7761-7766). In addition, the variable DNA population can be used to produce a population of RNA molecules with e.g. catalytic activities. Vaish et al., (PNAS. USA 1998 Mar. 3; 95 (5): 2158-2162) demonstrated the design of functional systems for the selection of catalytic RNA and Eckstein F (Ciba Found. Symp. 1997; 209; 207-212) has outlined the applications of catalytic RNA by the specific introduction of catalytic RNA in cells. The system may be used to further search through the sequence space in the selection of functional peptides/molecules with catalytic activities based on recombined DNA sequences.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

FIG. 1 shows the principle of the method from template molecule to improved molecule;

FIG. 2 shows the principle steps in preparation of single stranded DNA using biotin;

FIG. 3 shows the principle steps in the preparation of single stranded DNA using phage;

FIG. 4 shows the principle steps generating single stranded DNA fragments using exonuclease treatment;

FIG. 5 shows the principle steps for assembly of single stranded DNA fragments using PCR.

DETAILED DESCRIPTION AND EXEMPLIFICATION OF THE INVENTION

The DNA shuffling procedure can be illustrated by the steps shown in FIGS. 1-5. The gene encoding the protein of interest (X) in the plasmid pFab5chis is used in this example. Random mutations are introduced by error prone PCR. Single-stranded DNA is prepared. This can be carried out by either biotinylated primers or by the use of phage being able to pack single-stranded DNA, as discussed above. The coding and non-coding ssDNA strands are prepared in different reactions (A and B). The ssDNA strands from either reactions are subjected to separate enzymatic treatment using e.g. BAL 31. By mixing the two pools of single-stranded DNA fragments in equimolar amounts the gene can be resassembled in a shuffled nature and in many versions by the use of two subsequence PCR reactions, where the first reaction contains no primers. After cloning this library of reassembled genes in pY, selections can be performed to achieve the improved molecule of interest.

A more detailed description of examples of the present invention is given below.

Reagents:

AmpliTaq® polymerase was purchased from Perkin-Elmer Corp., dNTPs from Boehringer Mannheim Biochemica (Mannheim, Germany), and BAL31 Nuclease from New England Biolabs Inc. (Beverly, USA). All restriction enzymes were purchased from New England Biolabs Inc. (Beverly, USA). Ethidium bromide was purchased from Bio-Rad Laboratories (Bio-Rad Laboratories, Hercules, Calif., USA). T4 DNA Ligase was purchased from New England Biolabs Inc. (Beverly, USA). EDTA and EGTA was purchased from Kebo Lab (Sweden).

All primers were designed in the laboratory and obtained from Life Technologies (Täby, Sweden) and SGS-DNA (Köping, Sweden).

PCR:

All Polymerase Chain Reactions (PCR) were carried out in a automatic thermocycler (Perkin-Elmer Cetus 480, Norwalk, Conn., USA). PCR techniques for the amplification of nucleic acid are described in U.S. Pat. No. 4,683,195. References for the general use of PCR techniques include Mullis et al., Cold Spring Harbor Symp. Quant. Biol., 51: 263, (1987), Ehrlich (ed), PCR technology, Stockton Press, NY, 1989, Ehrlich et al., Science, 252: 1643-1650, (1991), "PCR protocols; A Guide to Methods and Applications", Eds. Innis et al., Academic Press, New York, (1990).

Sequencing:

All constructs have been sequenced by the use of BigDye Terminator Cycle Sequencing kit (Perkin-Elmer, Elmervill, Calif., USA). The sequencing was performed on a ABI Prism 377 DNA Sequencer.

Agarose Electrophoresis:

Agarose electrophoresis of DNA was performed with 2% agarose gels (AGAROSE (FMC Bioproducts, Rockland, Me., USA)) with 0.25 µg/ml ethidium bromide in Tris-acetate buffer (TAE-buffer 0.04M Tris-acetate, 0.001M EDTA). Samples for electrophoresis were mixed with a sterile filtrated loading buffer composed of 25% Ficoll and Bromphenolic blue and loaded into wells in a the 2% agarose gel. The electrophoresis was run at 90 V for 45 minutes unless otherwise stated in Tris-acetate buffer with 0.25 µg/ml ethidium bromide. Bands of appropriate size were gel-purified using the Qiaquick Gel Extraction Kit (Qiagen GmbH, Hilden, Germany) when needed. As molecular weight standard, DNA molecular weight marker 1 kb ladder (Gibco BRL) was used. The DNA-concentration of the gel extracted products were estimated using a spectrophotometer.

Bacterial Strains:

The *Escherichia coli*-strain TOP10F' was used as a bacterial host for transformations. Chemically competent cells of this strain were produced basically as described Hanahan, D. 1983. Studies on transformation of *Escherichia coli* with plasmids. J. Mol. Biol. 166: 557-580. Electrocompetent cells of this bacterial strain were produced (Dower, W. J., J. F. Miller, and C. W. Ragsdale. 1988: High efficiency transformation of *E. coli* by high voltage electroporation. Nucleic Acids Res. 16: 6127).

Plasmids:

All genetic manipulations were performed in pFab5chis according to Molecular cloning; a laboratory manual (Second Edition, Cold Spring Harbor Laboratory Press, 1989).

Primers:

Two biotinylated primers surrounding the antibody gene of pFab5chis were designed with the following sequences including designated unique restriction sites:

```
1736 SfiI forward primer (SEQ ID NO: 1):
5'-ATT ACT CGC GGC CCA GCC GGC CAT GGC CCA CAG GTC AAG CTC GA
and 1735 NotI reversed primer (SEQ ID NO: 2):
5'-TTA GAG CCT GCG GCC GCC TTG TCA TCG TCG TCC TT.
```

Two non-biotinylated primers surrounding the antibody gene of pFab5chis were designed with the following sequences including designated unique restriction sites:

```
1664 SfiI forward primer (SEQ ID NO: 1):
5'-ATT ACT CGC GGC CCA GCC GGC CAT GGC CCA CAG GTC AAG CTC GA
and 1635 NotI reversed primer (SEQ ID NO: 2):
5'-TTA GAG CCT GCG GCC GCC TTG TCA TCG TCG TCC TT.
```

Standard PCR:

Standard PCR reactions were run at 25 cycles consisting of following profile: denaturation (94° C., 1 minute), primer annealing (55° C., 1 minute) and extension (72° C., 3 minutes). Each PCR reaction contained 10 mM Tris-HCl, pH 8.3, 50 mM KCl, 1.5 mM $MgCl_2$, 200 µM dNTP, 1 µM forward primer, 1 µM reverse primer, 1.25 U AmpliTaq® thermostable DNA polymerase (Perkin-Elmer Corp.), and 50 ng template in a final volume of 100 µl.

Error Prone PCR:

The error prone PCR reactions were carried out in a 10× buffer containing 500 mM NaCl, 100 mM Tris HCl, pH 8.8, 5 mM $MgCl_2$ 100 µg gelatine (according to Kuipers et al., Nucleic Acids Res. 1991, Aug. 25; 19 (16):4558) except for a raise in the $MgCl_2$ concentration from 2 mM to 5 mM).

For each 100 µl reaction the following was mixed:

dATP 5 mM 5 µl dGTP 5 mM 5 µl dTTP 10 mM 10 µl dCTP 10 mM 10 µl

20 µM 3' primer 1.5 µl

20 µM 5'-primer 1.5 µl

10× Kuipers buffer 10 µl sterile mp $H_2O$ 46.3 µl

The template in pFab5chis vector was added at an amount of 50 ng. 10 µl of 10 mM $MnCl_2$ was added and the tube was checked that no precipitation of $MnO_2$ occurred. At last 5 Units of Taq enzyme was added. The error prone PCR was run at the following temperatures for 25 cycles without a hot start: 94° C. 1', 45° C. 1', 72° C. 1', +72° C. for 7 minutes. The resulting product was an error proned insert over the protein of approximately 750 bp. This insert was purified with Gibco PCR purification kit, before further treatment.

Generation of Single Stranded DNA by Biotinylated Primers

The fragment of interest was amplified by two separate PCR reactions. These reactions can be standard PCR as described above or error prone PCR also as described above. The primers should be designed so that in one reaction the forward primer is biotinylated and in the other reaction the reverse primer is biotinylated. For example, PCR reactions with A) primers 1736 and 1635 and B) primers 1664 and 1735, with the above mentioned profile was performed for 25 cycles with pFab5chis-antibody as template. This yielded PCR-products of approximately 750 bp where in A the upper strand was biotinylated and in B the lower strand was biotinylated.

The non-biotinylated strands were retrieved by purification using a solid matrix coated with streptavidin e.g. Dynabeads. The magnetic beads are washed and equilibrated with PBS/1% BSA and B&W buffer containing 5 mM Tris pH 7.5, 1 M NaCl, and 0.5 mM EGTA. 100 µl of each PCR product is mixed with 100 µl beads dissolved in 2×B&W buffer and incubated at room temperature for 15 minutes with rotation. Unbound PCR products are removed by careful washing twice with B&W. The non-biotinylated strand of the captured DNA is eluted by alkaline denaturation by letting the DNA incubate with 25 µl 0.1 M NaOH for 10 minutes in room temperature. The solution is separated from the beads and neutralized with 7.5 µl 0.33 M HCl and 2.5 µl 1 M Tris pH 8.

Generation of Single Stranded DNA Using Phage:

The fragment of interest was cloned into bacteriophage M13 vectors M13 mp18 and M13 mp19 using PstI/HindIII restriction enzymes. The bacteriophage were propagated using *Escherichia coli*-strain TOP10F' according to conventional methods. Single stranded DNA for the upper strand was prepared from bacteriophage vector M13 mp18 and single stranded DNA for the lower strand was prepared from bacteriophage vector M13 mp19. Briefly, 1.5 ml of an infected bacterial culture was centrifuged at 12 000 g for 5 minutes at 4° C. The supernatant was precipitated with 200 µl 20% PEG8000/2.5 M NaCl. The pelleted bacteriophage was resuspended in 100 µl TE. 50 µl phenol equilibrated with Tris-Cl (pH 8.0) was added and the sample was vortexed. After centrifugation at 12 000 g for 1 minute at RT the upper phase, containing the DNA, was transferred and precipitated with ethanol. The DNA pellet was dissolved in 50 µl TE (pH 8.0) and stored at −20° C. (Sambrook et al. Molecular Cloning, A laboratory manual $2^{nd}$ edition. Cold Spring Harbor Laboratory Press. 1989, chapter 4). Single stranded DNA prepared from phage is circular and must be opened prior to BAL31 treatment. This can be performed with an endonuclease able to cleave single stranded DNA.

Generation of Single Stranded Fragmented DNA Using BAL 31:

The ssDNA strands from either reactions (containing upper and lower strands, respectively) were subjected to separate enzymatic treatment using e.g. BAL 31. Each digestion reaction contained 0.02 µg/µl ssDNA, 600 mM NaCl, 20 mM Tris-HCl, 12 mM $CaCl_2$, 12 mM $MgCl_2$, 1 mM EDTA pH 8.0 and BAL 31 at various enzyme concentrations ranging from 0.1-5 U/ml. The reactions were incubated at 30° C. and fractions of digested ssDNA were collected sequentially at 10, 30, 60 and 120 seconds or longer. The reactions were stopped by addition of EDTA and heat treatment at 65° C. for 10 minutes. The ssDNA fragments were purified by phenol/chloroform extraction and ethanol precipitated. The ssDNA are resuspended in 10 mM Tris pH 8.0.

The digestion pattern was evaluated by 1% agarose gel electrophoresis.

Purification of Digestion Produced Fragments:

Digested DNA fragments were purified by phenol/chloroform/isoamylalcohol extraction. 50 µl of buffered phenol was added to each tube of 100 µl sample together with 50 µl of a mixture of chloroform and isoamylalcohol (24:1). The tubes were vortexed for 30 seconds and then centrifuged for 1 minute in a microfuge at 14000 r. p. m. The upper phase was then collected and mixed with 2.5 volumes of 99.5% Ethanol (1/10 was 3M Sodium Acetate, pH 5.2). The DNA was precipitated for 1 hour in 80° C. The DNA was then pelleted by centrifugation for 30 minutes in a microfuge at 14.000 r. p. m. The pellet was washed once with 70% ethanol and then re-dissolved in 10 µl of sterile water.

Analysis of Digestion Produced Purified Fragments on Agarose Gel:

5 µl of the dissolved pellet from each time point and from the blank were mixed with 2.5 µl of loading buffer (25% Ficoll and Bromphenolic blue) and loaded into wells in a 2% agarose gel. The electrophoresis of the different time points were performed as above.

Reassembly of Full Length Fragments:

Reassembly of the ssDNA fragments is achieved by two sequential PCR reactions. The first PCR reaction should contain 10 mM Tris-HCl, pH 8.3, 50 mM KCl, 1.5 mM $MgCl_2$, 200 µM dNTP, 0.3 U Taq polymerase and 2 µl BAL31 treated sample, all in a final volume of 25 µl, and subjected to 5 cycles with the following profile: 94° C. for 1 minute, 50° C. for 1 minute and 72° C. for 2 minutes+72° C. for 5 minutes. The second PCR reaction should contain 10 mM Tris-HCl, pH 8.3, 50 mM KCl, 1.5 mM $MgCl_2$, 200 µM dNTP, 0.6 U Taq polymerase, 1 µM forward primer, 1 µM reverse primer, and 5 µl sample from the first PCR reaction, all in a final volume of 50 µl, and subjected to 15 cycles with the following profile: 94° C. for 1 minute, 55° C. for 1 minute and 72° C. for 2 minutes+72° C. for 7 minutes. The resulting products can be evaluated by agarose gel electrophoresis.

Restriction Digestion of Reassembled Fragment and Plasmid with SfiI and NotI:

The reassembled fragment and the plasmid pFab5chis were first cleaved with SfiI by using NEB buffer 2 including BSA and 11 U enzyme/µg DNA. The reaction was carried out for 4 h at 50° C. After this the DNA was cleaved with NotI by adding conversion buffer and 6 U enzyme/µg DNA. This reaction was carried out for 37° C. overnight.

Gel Purification of Restriction Digested Vector and Restriction Digested Reassembled Fragment:

The cleavage reactions were analysed on a 1% agarose gel. The restriction digested insert showed a cleavage product of about 750 bp. This corresponds well with the expected size. The band of the cleaved insert and plasmid was cut out and gel-extracted as previously described.

Ligation of Reassembled Restriction Digested Fragment with Restriction Digested pFab5chis:

Purified cleaved pFab5chis was ligated with purified reassembled restriction digested fragment at 12° C. water bath for 16 hours. 50 µl of the vector was mixed with 50 µl of the insert and 15 µl of 10× buffer (supplied with the enzyme), 7.5 µl ligase (5 U/µl) and sterile water to a final volume of 150 µl. A ligation of restriction digested pFab5chis without any insert was also performed in the same manner.

Transformation of Chemically Competent *E Coli* TOP10F' with the Ligated Reassembled Insert and pFab5chis:

The ligation reactions were purified by phenol/chloroform extraction as described above. The upper phase from the extraction was collected and mixed with 2.5 volumes of 99.5% Ethanol (1/10 was 3M Sodium Acetate, pH 5.2). The DNA was precipitated for 1 hour in −80° C. The DNA was then pelleted by centrifugation for 30 minutes in a microfuge at 14.000 r. p. m. The pellet was washed once with 70% ethanol and then re-dissolved in 10 µl of sterile water. 5 µl of each ligation was separately mixed with 95 µl chemically competent *E coli* TOP10F' incubated on ice for 1 hour and then transformed (Sambrook et al. Molecular Cloning, A laboratory manual $2^{nd}$ edition. Cold Spring Harbor Laboratory Press, 1989). After one hour's growth the bacteria from the two transformations were spread onto ampicillin containing agar plates (100 µg/ml). The plates were grown upside-down in a 37° C. incubator for 14 hours.

The invention claimed is:

1. A method for generating a polynucleotide sequence or population of sequences from parent single stranded polynucleotide sequences encoding one or more protein motifs, comprising the steps of
   a) providing single stranded DNA constituting plus and minus strands of parent polynucleotide sequences;
   b) digesting the single stranded polynucleotide sequences with a nuclease other than DNase I to generate populations of single stranded fragments;
   c) contacting said fragments generated from the plus strands with fragments generated from the minus strands and optionally, adding primer sequences that anneal to the 3' and 5' ends of at least one of the parent polynucleotides under annealing conditions;
   d) amplifying the fragments that anneal to each other to generate at least one polynucleotide sequence encoding one or more protein motifs having altered characteristics as compared to the one or more protein motifs encoded by said parent polynucleotides.

2. A method as claimed in claim 1 wherein the nuclease other than DNase I is an exonuclease.

3. A method as claimed in claim 2 wherein the exonuclease is BAL31.

4. A method as claimed in claim 1 wherein a parent polynucleotide sequence or sequences has been subjected to mutagenesis.

5. A method as claimed in claim 1 wherein the population of fragments generated in step b) are subjected to mutagenesis.

6. A method as claimed in claim 4 wherein the mutagenesis is error prone PCR.

* * * * *